(12) United States Patent
Javaud et al.

(10) Patent No.: US 8,574,871 B2
(45) Date of Patent: Nov. 5, 2013

(54) GENETICALLY MODIFIED YEASTS FOR THE PRODUCTION OF HOMOGENOUS GLYCOPROTEINS

(75) Inventors: Christophe Javaud, Brive (FR); Vincent Carre, Jabreilles-les-Bordes (FR)

(73) Assignee: GLYCODE, Uzerche (FR)

( * ) Notice: Subject to any disclaimer, the term of this patent is extended or adjusted under 35 U.S.C. 154(b) by 810 days.

(21) Appl. No.: 12/525,661

(22) PCT Filed: Jan. 25, 2008

(86) PCT No.: PCT/EP2008/050888
§ 371 (c)(1),
(2), (4) Date: Dec. 10, 2009

(87) PCT Pub. No.: WO2008/095797
PCT Pub. Date: Aug. 14, 2008

(65) Prior Publication Data
US 2010/0137565 A1    Jun. 3, 2010

(30) Foreign Application Priority Data

Feb. 2, 2007   (FR) .................... 07 53050

(51) Int. Cl.
*C12N 1/19*      (2006.01)
(52) U.S. Cl.
USPC ... 435/69.1; 435/69.4; 435/69.6; 435/254.21; 435/477; 435/483; 530/322
(58) Field of Classification Search
None
See application file for complete search history.

(56) References Cited

U.S. PATENT DOCUMENTS

| | | | |
|---|---|---|---|
| 2004/0018588 A1 | 1/2004 | Contreras et al. | |
| 2005/0106664 A1 | 5/2005 | Contreras et al. | |
| 2008/0009037 A1 | 1/2008 | Contreras et al. | |

FOREIGN PATENT DOCUMENTS

| | | |
|---|---|---|
| WO | 2004/003194 A | 1/2004 |
| WO | 2005/049807 A | 6/2005 |

OTHER PUBLICATIONS

Alani et al., Genetics 116: 541-545 (1987).*
Vervecken, W. et al., "In Vivo Synthesis of Mammalian-Like, Hybrid-Type N-Glycans in Pichia Pastoris," Applied and Environmental Microbiology, Washington, DC, US, vol. 70, No. 5. May 2004 pp. 2639-2646, XP008032109, ISSN: 0099-2240.
Chiba Yasunori et al: "Production of human compatible high mannose-type (Man5GlcNAc2) sugar chains in *Saccharomyces cerevisiae*" Journal of Biological Chemistry, American Society of Biolochemical Biologists, Birmingham, US, vol. 273, No. 41, Oct. 9, 1998, pp. 26298-26304, XP002202331, ISSN: 0021-9258.
Hamilton, Stephen R. et al: "Humanization of yeast to produce complex terminally sialylated glycoproteins," Science, American Association for the Advancement of Science, US, vol. 313, No. 5792. Sep. 2006, pp. 1441-1443, XP002457470, ISSN: 0036-8075.
Hamilton, S. R. et al.: "Production of complex human glycoproteins in yeast", Science, American Association for the Advancement of Science, US, vol. 301, No. 5637, Aug. 29, 2003), pp. 1244-1246, XP002267832, ISSN: 0036-8075.
Suihko M-L et al: "Construction and Analysis of Recombinant Glucanolytic Brewer's Yeast Strains," Applied Microbiology and Biotechnology, Springer Verlag, Berlin, DE, vol. 35, No. Sep. 6, 1991, pp. 781-787, XP000982895, ISSN: 0175-7598.
Taxis, Christof; Knop, Michael: "System of centromeric, episomal, and integrative vectors based on drug resistance markers for *Saccharomyces cerevisiae*," Biotechniques, vol. 40, No. 1. Jan. 2006), pp. 73-78, XP001537899.

* cited by examiner

*Primary Examiner* — Jim Ketter
(74) *Attorney, Agent, or Firm* — Harness, Dickey & Pierce, P.L.C.

(57) ABSTRACT

The present application relates to genetically modified yeasts for the production of glycoproteins having optimized and homogeneous glycan structures. These yeasts comprise an inactivation of the Och 1 gene, the integration by homologous recombination, into an auxotrophic marker, of an expression cassette comprising a first promoter, and an open reading frame comprising the coding sequence for an α-1,2-mannosidase I, and the integration of a cassette comprising a second promoter different from said first promoter and the coding sequence for an exogenous glycoprotein. These yeasts make it possible to produce EPO with an optimized and 98% homogeneous glycosylation.

27 Claims, 8 Drawing Sheets

GENETICALLY MODIFIED YEASTS FOR THE PRODUCTION OF HOMOGENOUS GLYCOPROTEINS

CROSS-REFERENCE TO RELATED APPLICATIONS

This application is a National Phase Entry of International Application No. PCT/EP2008/050888, filed on Jan. 25, 2008, which claims priority to French Patent Application No. 0753050, filed on Feb. 2, 2007, both of which are incorporated by reference herein.

BACKGROUND

The present invention relates to genetically modified yeasts for producing glycoproteins having optimized and homogeneous glycan structures. These yeasts comprise inactivation of the Och1 gene, integration by homologous recombination into an auxotrophy marker of an expression cassette comprising a first promoter, and an open reading phase comprising the sequence coding for an α-1-2 mannosidase I, and integration of a cassette comprising a second promoter different from said first promoter and the sequence coding for an exogenous glycoprotein. These yeasts allow production of EPO with optimized and homogeneous 98% glycosylation.

The production of glycoproteins or glycopeptides having glycans of the complex type, i.e. structures identical with oligosaccharides added during post-translational modifications in humans, has been a sought goal for quite a few years in the pharmaceutical industry. Indeed, many studies have shown the importance of oligosaccharides for optimizing the activity of therapeutic glycoproteins or further for improving their half-life time once they are administered. For example, human erythropoietin (HuEPO) is a glycoprotein of 166 amino acids containing three N-glycosylation sites in positions Asn-24, Asn-38 and Asn-83 and an O-glycosylation site of the mucin type in position Ser-126. EPO is a particularly relevant model for studying N-glycosylation because of its glycosylated structures representing 40% of its molecular weight. The EPO molecule considered as natural is the urinary form (uHuEPO) (Takeuchi et al., 1988, Tusda 1988, Rahbeck-nielsen 1997). Recombinant EPO (rHuEPO) is presently produced in CHO cells (Sasaki H et al., Takeuchi et al., 1988) or in BHK cells (Nimtz et al., 1993). The rHuEPOs expressed in cell lines have N-glycan structures different from the structures found in uHuEPO. These differences may have repercussion in vitro (Higuchi et al., 1992; Takeuchi et al., 1990) but seem to be more sensitive in vivo by a drastic loss of activity for the deglycosylated forms and by an increase of activity correlated with the number of sialic acids present on the structure (Higuchi M et al., 1992).

In order to produce glycoproteins having optimum N- or O-glycosylation, many technical solutions have been proposed. Mention may be made of in vitro modifications of glycan structures by adding sugars such as galactose, glucose, fucose or even sialic acid by means of different glycosyl transferases or by suppressing certain sugars such as mannose with mannosidases. This technique is described in WO 03/031464 (Neose). It is however possible to wonder how such a technique may be applied on a large scale since this involves many steps for sequential modification of several given oligosaccharides present on a same glycoprotein. In each step, strict control of the reaction should be carried out and production of homogeneous glycanic structures should be ensured. Now, in the case when many oligosaccharides have to be modified on a glycoprotein, a sequential reaction may result in undesirable and heterogeneous modifications. This technique is therefore not compatible with the preparation of biodrugs. Further, the use of purified enzymes for production on an industrial scale does not seem to represent a viable economical alternative.

The same applies with chemical coupling techniques, such as those described in documents WO 2006/106348 and WO 2005/000862. These chemical coupling techniques involve tedious reactions, protection/deprotection steps, multiple checks. In the case when many oligosaccharides have to be modified on a given glycoprotein, a sequential reaction may also result in undesirable and heterogeneous modifications. Other technologies using mammal cell lines such as YB2/0 described in WO 01/77181 (LFB) or further CHO lines genetically modified in WO 03/055993 (Kyowa) have demonstrated that slight fucosylation of the Fc region of the antibodies improves ADCC activity by a factor 100. However, these technologies specifically relate to the production of antibodies.

Finally, production of glycoproteins in yeasts or filamentous fungi has been proposed by transformation of these micro-organisms with plasmids allowing expression of mannosidases and of different glycosyl transferases. This approach was described in WO 02/00879 (Glycofi). However, to this day, it has not been demonstrated that these micro-organisms are stable over time in a high capacity fermenter for producing clinical batches. Also, it has not been shown that this transformation enables production of glycoproteins with the desired and homogeneous glycans.

With the purpose of producing rHuEPO having N-glycan structures with which optimum activity may be obtained in vivo, we expressed an rHuEPO in genetically modified *S. cerevisiae* and *S. pombe* yeasts. These yeasts showed strong expression of rHuEPO having homogeneous and well-characterized N-glycosylation units. In a second phase, we started with genetically modified yeasts and we incorporated other modifications in order to produce more complex N-glycan units, depending on their sialylation levels. The yeast system is known for its capacity of rapidly producing a large amount of proteins but the modified yeasts described hereafter are also capable of N-glycosylation of the produced proteins in a "humanized" and homogeneous way. Further, these yeasts are found to be stable under conditions of production on a large scale. Finally, in the case of mutations leading to genotype reversion, these yeasts are constructed so as to allow them to be restored identically, which is required within the scope of producing clinical batches.

Thus, this is the first example which illustrates targeted integration methods in particular loci which have been used for the whole of the invention, methods allowing control of interrupted and selected genome regions to within one nucleotide, and therefore allowing restoration of the interruption in the case of spontaneous genome reversion. This method should be opposed to the one described in WO 02/00879, consisting of transforming a yeast strain with a bank of sequences and subsequently selecting the best clone without any genomic characterization. Indeed, in WO 02/00879 the integrations are random and the clones are exclusively selected on the basis of the profile of N-glycan structures of the produced proteins, which involves, in the case of mutations, reversion or any other genetic modification, pure and simple loss of the clone of interest. The advantage of the technology according to the invention is to provide increased safety to the user, by providing him/her with a guarantee of controlling, tracking genetic modifications, and especially the possibility of reconstructing a clone which will strictly have the same capacities.

Further, for the first time we provide a "Glycan-on-Demand" technology from the Amélie strain as described hereafter. Under these conditions, the homogeneity of the structures is more important than in the CHO systems which glycosylate like mammals. Indeed, the obtained results (see EPO spectrum), report a glycan structure of the Man5GlcNAc2 type representing about 98% of the N-glycans present on the protein. The system is therefore designed so as to force glycosylation in order to obtain a desired unit in very large proportion. The Amélie strain is the clone used as a basis for elaborating any other strain intended to produce humanized, hybrid or complex glycans, which one wishes to obtain. The advantage of this strain is to form a starting point, which was demonstrated as being a stable and homogeneous system producing 98% of Man5GlcNAc2 glycoproteins, which may be reworked for additional modifications such as the introduction of a GlcNAc transferase, of a fucosyl transferase, of a galactosyl and/or sialyl transferase, on demand, rapidly, according to the desired final structures.

SUMMARY

The construction of an expression cassette is carried out by integrating a promoter sequence in position 5' and a terminal sequence in position 3' of the ORF. On the other hand, the integration of these cassettes into the genome of the yeasts is controlled by adding to the ends, sequences homologous to the target locus with the purpose of integration by homologous recombination. For each strain and for each ORF, the promoter sequences as well as the integration sequences, have been determined with the purpose of obtaining stable and optimum expression of the different enzymes allowing homogeneous glycosylation of glycoproteins. The construction of an expression cassette is accomplished in several successive pCR steps, according to this general model shown in FIG. 2 (assembly PCR for constructing expression cassettes of the ORFs). Certain ORF sequences have been partly modified by integrating sub-cellular localization signals in order to express (address) the protein in a compartment where its activity will be optimum (environment, presence of the donor, and of the substrates, etc. . . . ).

Thus, in a first aspect, the present invention relates to genetically modified yeasts, capable of producing glycoproteins having homogeneous glycans having the structure Man5GlcNAc2, said yeasts comprising the following modifications:
a) inactivation of the Och1 gene coding for α-1,6-mannosyl transferase by insertion by homologous recombination of a heterologous sequence coding for a gene of resistance to an antibiotic (kanamycin) (delta-Och1 strain),
b) integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for an α-1-2-mannosidase I comprising a targeting sequence in the endoplasmic reticulum or the Golgi apparatus and a terminator of the transcription,
c) integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, said promoter in c) being different from the promoter in b); an open reading phase comprising the sequence coding for an exogenous glycoprotein to be produced and a terminator of the transcription.

Preferably, the yeasts described above have integrated α-1-2 mannosidase I of C. Elegans, notably a sequence comprising SEQ ID NO 1. These yeasts are found to be capable of producing glycoproteins having 98% of Man5GlcNac2 glycans:

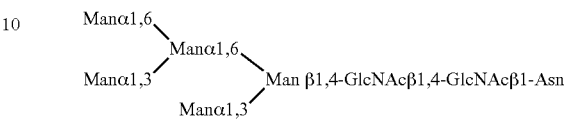

Advantageously, α-1-2 mannosidase I is expressed under the control of the promoter pGAP and the exogenous protein glycoprotein is expressed under the control of the promoter pGAL1. In the following description, reference will be made to the abbreviations used in the state of the art Man=mannose, GlcNac=N-acetyl-glucosamine, Gal=galactose, Fuc=fucose and NANA designating sialic acid or further N-acetylneuraminic acid.

In a second aspect, the yeasts of the invention include additional modifications in order to produce glycoproteins having more than 75%, or even 80% or further 95% or 98% of the GlcNacMan5GlcNAc2 structure:

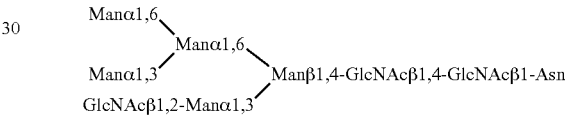

For this purpose, the above strains further comprise integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for human N-acetyl-glucosaminyl transferase I, comprising a targeting sequence in the endoplasmic reticulum or the Golgi apparatus and a terminator of the transcription. Preferably, human N-acetyl-glucosaminyl transferase I comprises the sequence SEQ ID NO 2 without the cytoplasmic portion of the enzyme which is replaced with the cytoplasmic portion of Mnn9 for Golgian localization of the protein. This strain is designated as "Arielle". Arielle should also contain the GlcNAc UDP transporter cassette (described below) in order to synthesize this type of glycan. Advantageously, the promoter pGAP is used.

Mnn9
(SEQ ID NO 13)
<u>Atgtcactttctcttg</u>tatcgtaccgcctaa<u>gaaagaacccgtgggttta</u>

<u>ac</u>: cytoplasmic portion.

The Amélie strain above may further comprise integration by homologous recombination into an auxotrophy marker of an expression cassette comprising a promoter pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for the cassette for the human UDP-GlcNAc transporter and a terminator of the transcription.

Preferably, the human UDP-GlcNAc transporter comprises the sequence SEQ ID NO 3. Preferably the promoter is PGK. This strain is designated hereafter as "Agathe".

In a third aspect, the yeasts of the invention include additional modifications in order to produce glycoproteins having more than 75%, or even 80% or further 95% or 98% of the GlcNacMan3GlcNAc2 structure:

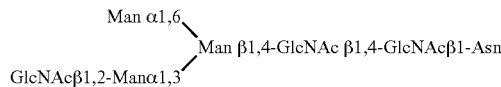

As such, the Arielle yeasts mentioned above comprise integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for a mannosidase II comprising a targeting sequence in the endoplasmic reticulum or the Golgi apparatus and a terminator of the transcription. Preferably, mannosidase II is that of mice, notably a sequence comprising SEQ ID NO 4. Preferably the promoter is TEF. This strain is designated hereafter as "Anaïs".

In a fourth aspect, the yeasts of the invention include additional modifications in order to produce glycoproteins having more than 75%, or even 80% or further 95% or 98% of the GlcNac2Man3GlcNAc2 structure:

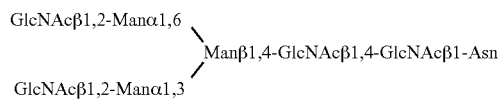

In this case, the Anaïs yeasts mentioned above comprise integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID No 16-26 respectively, an open reading phase comprising the sequence coding for an N-acetyl-glucosaminyl transferase II, comprising a targeting sequence in the endoplasmic reticulum or the Golgi apparatus and a terminator of the transcription. Preferably, the N-acetyl-glucosaminyl transferase II is human, notably a sequence comprising SEQ ID NO 5. Preferably the promoter is PMA1, this strain is designated hereafter as "Alice".

In another embodiment, the Alice yeasts of the invention include additional modifications in order to produce glycoproteins having more than 75%, or even 80% or further 95% or 98% of the Gal2GlcNac2Man3GlcNAc2 structure:

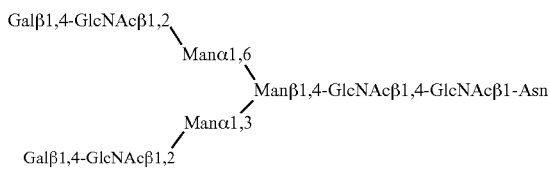

In this case, the Alice yeasts mentioned above comprise integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, preferably the promoter CaMV, an open reading phase comprising the sequence coding for a galactosyl transferase I, comprising a targeting sequence in the endoplasmic reticulum or the Golgi apparatus and a terminator of the transcription. Preferably, the galactosyl transferase I is human, notably a sequence comprising SEQ ID NO 6, which is without the human targeting sequence. This strain is designated as "Athena".

Advantageously, the integration of the aforementioned expression cassettes is carried out in an integration marker selected from (auxotrophy marker selected from) URA3, ADE2, LYS2, LEU2, TRP1, CAN1, ADO1, HIS5, HIS3, ARG3, MET17, LEM3, Mnn1, Mnn9, gma12. Even more advantageously, the expression cassette of α-1-2 mannosidase I is integrated into the URA3 gene, the expression cassette of N-acetyl-glucosaminyl transferase I is integrated into the ADE1 or ADE2 gene, the expression cassette of the UDP-GlcNAc transporter is integrated into the LYS2 gene, the expression cassette of α-mannosidase II is integrated in the LEU2 gene, and the expression cassette of N-acetyl-glucosaminyl transferase II is integrated into the LEM3 or TRP1 gene. The expression cassette of β-1,4-galactosyl transferase I is integrated into TRP1 or MET17. Further, a targeting sequence in the endoplasmic reticulum or the Golgi apparatus, derived from the localization sequence of the Mnt1 gene which comprises the sequence SEQ ID NO 14 and the terminator CYC1 comprising the SEQ ID NO 15, is preferably used in the constructs.

In another embodiment, the yeasts Alice and Athena, described above, of the invention, include additional modifications in order to produce glycoproteins having more than 75%, or even 80% or further 95% or 98% of a structure selected from
GlcNac2Man3GlcNAc2,
Gal2GlcNac2Man3GlcNAc2, and
GlcNac2Man3(Fuc)GlcNAc2, Ashley strain
Gal2GlcNac2Man3(Fuc)GlcNAc2, Aurel strain In this case, the yeasts mentioned above comprise integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, or the promoter of the nmt1 gene, an open reading phase comprising the sequence coding for an α-1,6-fucosyl transferase FUT8, comprising a targeting sequence in the endoplasmic reticulum or the Golgi apparatus and a terminator of the transcription, in particular the terminator derived from the CYC1 gene. These strains may advantageously contain the cassette corresponding to the GDP-fucose transporter described below. This cassette may be integrated into CAN1 or HIS5.

Preferably, the α-1,6-fucosyl transferase FUT8 is human, notably a sequence comprising SEQ ID NO 7. Further, this strain should comprise integration by homologous recombination into an auxotrophy marker of an expression cassette comprising the promoter SV40, and open reading phase comprising the sequence coding for a GDP-fucose transporter, notably a sequence comprising SEQ ID NO 8. This cassette may be integrated in TRP1, ARG3 or gma12.

In another embodiment, the yeasts GlcNac2Man3GlcNAc2 (Athena) and Gal2GlcNac2Man3 (Fuc)GlcNAc2 (Aurel) described above of the invention, include additional modifications in order to produce glycoproteins having more than 75%, or even 80% or further 95% or 98% of a structure selected from
NANA2Gal2GlcNac2Man3GlcNAc2 Aeron strain
NANA2Gal2GlcNac2Man3(Fuc)GlcNAc2 Avrel strain GlcNac2Man3GlcNAc2,
Gal2GlcNac2Man3GlcNAc2,
NANA2Gal2GlcNac2Man3GlcNAc2,
GlcNac2Man3(Fuc)GlcNAc2,

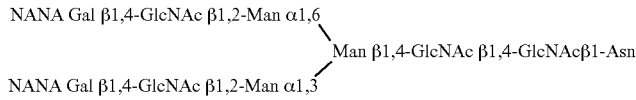

In this embodiment, the yeasts mentioned above comprise integration by homologous recombination into an auxotrophy marker of an expression cassette comprising a promoter among those mentioned above or the promoter of the thymidine kinase of the herpes virus comprising the sequence SEQ ID NO 9. An open reading phase comprising the sequence coding for an α-2,3-sialyl transferase (ST3GAL4 gene) and a terminator of the transcription, in particular the terminator derived from the CYC1 gene comprising the sequence SEQ ID NO 15. Preferably the sialyl transferase is human (NM_006278), notably a sequence comprising SEQ ID NO 10.

In another embodiment, the yeasts Gal2GlcNac2Man3GlcNAc2 (Athena) and NANA2Gal2GlcNac2MAN3GLCNAc2 (Aeron) described above of the invention include additional modifications in order to produce glycoproteins having more than 75%, or even 80%, or further 95% or 98% of a structure selected from
Gal2GlcNac3Man3GlcNAc2 Azalée strain
NANA2Gal2GlcNac3Man3GlcNAc2 A strain Gal2GlcNac2Man3(Fuc)GlcNAc2,
NANA2Gal2GlcNac2Man3GlcNAc2,
Gal2GlcNac2Man3GlcNAc2,
NANA2Gal2GlcNac3Man3GlcNAc2, The invention also relates to a pharmaceutical composition comprise EPO as an active ingredient, said EPO having more than 75%, 90%, 95% or further 98% of the structure NANA2Gal2GlcNac2Man3GlcNAc2 or NANA2Gal2GlcNac2Man3(Fuc)GlcNAc2

The invention also relates to a culture in a fermenter comprising a basic culture medium of culture media for yeasts and to a yeast described above.

In still another aspect, the invention relates to a method for producing a glycoprotein having homogeneous glycan structures with more than 75%, 90%, 95% or further 98% of the structure
Man5GlcNAc2,
GlcNacMan5GlcNAc2,
GlcNacMan3GlcNAc2,

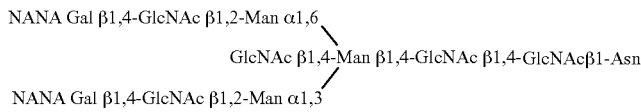

In this embodiment, the yeasts mentioned above comprise integration by homologous recombination into an auxotrophy marker of an expression cassette comprising a promoter from those mentioned above. An open reading phase comprising the sequence coding for a β-1,4-n-acetyl-glucosaminyl transferase III and a terminator of the transcription, in particular the terminator derived from the CYC1 gene comprising the sequence SEQ ID NO 15. Preferably the GNTIII is murine, notably a sequence comprising SEQ ID NO 27.

As indicated above, the yeasts according to the invention are integrated into a cassette for expressing an exogenous glycoprotein or glycopeptide. The glycoprotein may be selected from glycoproteins for therapeutic use such as cytokines, interleukins, growth hormones, growth factors, enzymes, and monoclonal antibodies, vaccinal proteins, soluble receptors and all types of recombinant proteins. This may be a sequence coding for EPO, notably a cassette comprising SEQ ID NO 11 coding for an EPO with SEQ ID NO 12 comprising the epitope V5 and an N-terminal poly-HIS unit for purification.

The invention also relates to a pharmaceutical composition comprising a glycoprotein having homogeneous glycan structures of more than 75%, 90%, 95% or further 98% of the structure:
Man5GlcNAc2,
GlcNacMan5GlcNAc2,
GlcNacMan3GlcNAc2,
GlcNac2Man3GlcNAc2,
Gal2GlcNac2Man3GlcNAc2,
NANA2Gal2GlcNac2Man3GlcNAc2,
GlcNac2Man3(Fuc)GlcNAc2,
Gal2GlcNac2Man3(Fuc)GlcNAc2,
NANA2Gal2GlcNac2Man3(Fuc)GlcNAc2,
Gal2GlcNac3Man3GlcNAc2,
NANA2Gal2GlcNac3Man3GlcNAc2
comprising the cultivation of a yeast as described above in a fermenter, and the extraction of said glycoprotein from the culture medium. This method may comprise a purification step.

Finally, the invention also relates to the use of a yeast as described above for producing in a fermenter a glycoprotein having homogeneous glycan structures with more than 75%, 90%, 95% or further 98% of the structure
Man5GlcNAc2,
GlcNacMan5GlcNAc2,
GlcNacMan3GlcNAc2,
GlcNac2Man3GlcNAc2,
Gal2GlcNac2Man3GlcNAc2,
NANA2Gal2GlcNac2Man3GlcNAc2,
GlcNac2Man3(Fuc)GlcNAc2,
Gal2GlcNac2Man3(Fuc)GlcNAc2,
NANA2Gal2GlcNac2Man3(Fuc)GlcNAc2,
Gal2GlcNac3Man3GlcNAc2,
NANA2Gal2GlcNac3Man3GlcNAc2

DETAILED DESCRIPTION

Example 1

Creation of Mutated Strains on the Och1 Gene Coding for α-1,6-Mannosyl Transferase (Delta-Och1 Strain)

Figure 1:
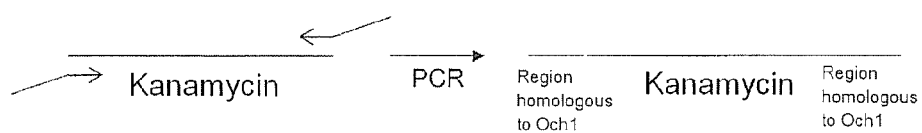
FIG. 1: PCR-based construction of an OCH1-inactivating cassette.

The gene for resistance to kanamycin was amplified by PCR and homologous flanking regions to the gene Och1 were added in both of these ends (FIG. 1), specific regions of each strain of S. cerevisiae or S. pombe yeast. The gene Och1 is made non-functional by inserting this gene for resistance to an antibiotic, kanamycin. Integration of the gene into the genome of the yeast is accomplished by electroporation and the gene of interest is then integrated by homologous recombination. The flanking regions have about forty bases and allow integration of the kanamycin gene within the gene Och1 in the genome of the yeast.

The strains having integrated the gene for resistance to kanamycin are selected on the medium containing 50 µg/mL of kanamycin. We then checked by PCR the integration of the gene for resistance to kanamycin in the gene Och1. Genomic DNA of the clones having resisted to the presence of kanamycin in the medium, was extracted. Oligonucleotides were selected so as to check the presence of the gene for resistance to kanamycin on the one hand and that this gene was actually integrated into the Och1 gene on the other hand. Genomic DNA of wild strains was also tested; we amplified the Och1 gene of these strains. This gene has 1,100 bp. In the strains having integrated the kanamycin cassette, the observed amplification of the gene Och1 is longer (1,500 bp).

Example 2

Tests of Activities 2.1 Och1 Mannosyl Transferase Activity on Strains of Mutated Yeasts Another validation level: for each gene integrated to the genome of the yeast strains, systematic check of the enzymatic activity was carried out, in order to constantly follow possible fluctuations in the activity levels, due for most of the time to spontaneous mutations and then requiring selection of new clones.

The activity of the Och1 enzyme may be detected by an assay in vitro. Prior studies have shown that the best acceptor for transfer of mannose by the Och1 enzyme is Man$_8$GlcNAc$_2$. From microsomal fractions of yeasts (100 µg of proteins) or from a lysate of total proteins (200 µg), the transfer activity of mannose in the alpha-1,6 position on a Man$_8$GlcNAc$_2$ structure is measured. For this, the Man$_8$GlcNAc$_2$ coupled to an amino-pyridine group (M$_8$GN$_2$-AP) is used as an acceptor and the GDP-mannose marked with [$^{14}$C]-mannose as a donor molecule of radioactive mannose. The microsomes or the proteins are incubated with the donor (radioactive GDP-mannose), the acceptor (Man$_8$GlcN$_2$-AP) and deoxymannojirimycin (inhibitor of mannosidase I) in a buffered medium with controlled pH. After 30 minutes of incubation at 30° C., chloroform and methanol are added to the reaction medium in order to obtain a proportion of CHCl$_3$/MeOH/H$_2$O of 3:2:1 (v/v/v). The upper phase corresponding to the aqueous phase, contains Man$_8$GlcNAc$_2$-AP, radioactive Man$_9$GlcNAc$_2$-AP and GDP-[$^{14}$C]-mannose. Once dried, the samples are taken up in 100 µL of H$_2$O/1% acetic acid and passed over a Sep-Pak C18 (Waters) column, conditioned beforehand in order to separate GDP-mannose from the formed radioactive Man$_9$GlcNAc$_2$-AP (the AP group allows this compound to be retained on the C18 columns). By eluting with H$_2$O/1% acetic acid (20 mL) and then with 20% methanol/1% acetic acid (4 mL), the different fractions may be recovered and counted with the scintillation counter.

2.2 Mannosidase Activity

Mannosidase activity is measured by incubating for 4 hours at 37° C., with 4 mM of p-nitrophenyl-α-D-mannopyranoside with 100-200 µg of proteins (from total proteins or sub-cellular fractions) in 0.1 M of PBS, pH 6.5+/−120 µM DMJ (alpha-1,2-mannosidase I inhibitor) +/−12 µM SW (specific inhibitor of mannosidase II). Absorbance is measured at 405 nm.

2.3 N-Acetylglucosaminyl Transferase Activity

GlcNAc transferase activity is measured on microsomal fractions of yeasts. 50 µg of microsomes (BCA assay) are incubated in finally 50 µL after 25 minutes at 30° C. with 0.01 µCi of donor (radioactive UDP-GlcNAc), 0.5 mM of acceptor (3-O-α-D-manno-pyranosyl-D-mannopyranoside) in a medium with 50 mM HEPES, 10 mM MnCl$_2$, 0.1% TritonX-100. The reaction is stopped with 400 µL of 10 mM EDTA and the samples are then passed over Dowex AG-1X2 columns. The radioactive acceptor is then eluted from the columns with 3M formic acid and the radioactivity is measured with a scintillation counter.

Example 3

Expression Cassette for α-1-2 Mannosidase I of *C. Elegans*

Figure 2:
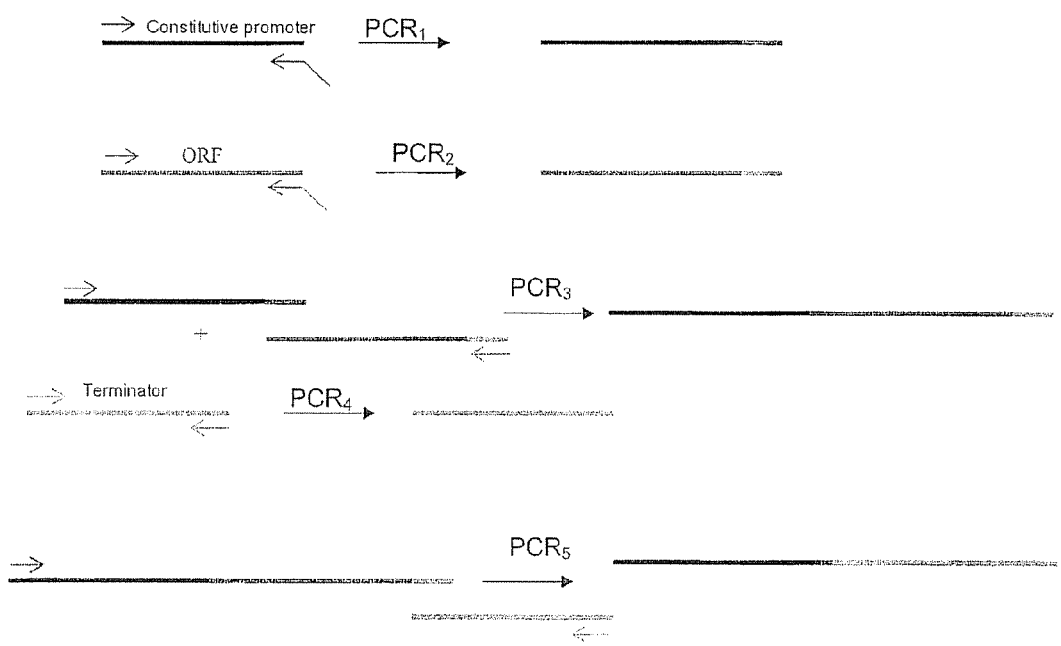
FIG. 2: Construction of expression cassettes.

Explanatory diagram for constructing expression cassettes: FIG. 2.

3.1 Step 1: Obtaining the ORF

α-mannosidase I: PCR from bacterial clones having the plasmid pDONR201

(Open Biosystem)

Program:

---
8 minutes at 94° C.
35 cycles: 20 s at 94° C.
30 s at 65° C.
2 min at 72° C.
10 minutes at 72° C.
---

Amplification of a 1,644 by fragment (SEQ ID No 1)
```
AAAGCAGGCatgggcctccgatcacacgaacaacttgtcgtgtgtgcgg
agttatgtttcttctgactgtctgcatcacagcgttt ttctttcttccgtcaggcggcgctgatctgtatttccgagaagaaaactc
cgttcacgttagagatgtgcttatcagagaggaaatt cgtcgtaaagagcaagatgagttacggcggaaagccgaagaagccaatcc
cattccaattccaaaacctgaaattggagcat cagatgatgcagaaggacgaagaattttcgtgaaacaaatgattaaattc
gcatgggacggatatcggaaatatgcctggggg gagaatgaattgaggcccaacagtagatcaggacattcttcatcgatatt
tgggtatggaaagacgggtgcaacaattattgatg ctattgatacattgtatttggttggattaaaagaagaatataaagaggcc
agagactggattgctgattttgatttcaaaacgtctgc gaaaggagatctatcagttttgaaacaaatatccgattcactggtggcc
tactctccgcatttgcacttaccggagacaaaatgtt cttgaagaaagcagaagatgtggcaactattcttcttccggcttttgaaa
ctccttctggaataccaaattcattaattgatgctcaa acaggaagatccaaaacgtatagttgggcaagcggaaaggcaattctctc
ggaatacggttcaattcaacttgaattcgattatc tctccaatctgactggaaatccagttttttgctcaaaaagctgataaaata
agagatgttttaactgcaatggagaaaccagaagg actttatccaatttatattactatggataatccaccaagatggggacaac
atcttttctcaatgggtgcaatggctgacagttggtat gaatatctgctcaaacaatggattgccactggtaaaaaagatgatcgcac
gaaaagagaatacgaagaagcgatatttgcaat ggaaaaacgaatgcttttcaaatcggaacagtcgaatctttggtatttcg
caaaaatgaacggaaatcgcatggaacattcatttg aacatcttgcatgcttttccggtggaatggttgttcttcatgcaatgaat
gagaaaaataaaacaatatcagatcattatatgacgtt gggaaaagaaattggtcatacatgtcatgaatcgtacgctagatccacaa
ctggaatcggcccagaatccttccaattcacatc gagtgtagaggcaaaaacagaacgtcgtcaggattcatattatattcttc
gtcctgaagtcgttgagacatggttctacttgtgga
```
-continued
```
gggctacaaaagacgagaaatatcgacaatgggcttgggatcatgttcaa
aatttggaggagtattgtaagggcactgccgga tactctggaatccgaaacgtctacgaatcgagcccggaacaagatgatgt
gcagcagtcattcctcttcgctgagctcttcaaat atctgtatttaattttcagtgaagataacattcttccacttgatcaatgg
gttttcaataccgaagctcatccattccgcattcggcatcacgacgagtt
gatt
```

The PCR amplification was extracted and purified from agarose gel with SBIOgene kit and was introduced into a vector TOPO2.1. Competent bacteria (TOP10, Invitrogen) were transformed with this vector. The transformation was checked by PCR and insertion of the PCR amplification into the vector by sequencing (plasmid pGLY02.001).

3.2 Step 2: Assembling the Expression Cassette

Integration of the expression cassette of mannosidase I will be localized in the auxotrophy marker URA3 for both strains. Invalidation of this gene induces resistance to a toxic agent, 5-fluorouracil. Yeasts modified by this cassette will then become resistant to this drug but also auxotrophic for uracil.

Expression Cassette for *S. Cerevisiae*

Amplification of the promoter pGAP from genomic DNA of wild *S. cerevisiae* BS16 (forward) and BS17' (reverse)

Assembling the promoter pGAP (PCR product) and the ORF (pGLY02.001) BS16 (forward) and BS19' (reverse)

Amplification of the terminator CYC1 from the plasmid pYES 2.1 BS40b (forward) and BS41 (reverse)

Assembling the ORF (plasmid pGLY02.001) and the terminator CYC1 (PCR product)

BS18 (forward) and BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY02.002).

Assembling promoter-ORF (PCR product) and ORF-terminator (pGLY02.002) with regions homologous to URA3 (from the primers)

BS42 (forward)

BS43 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY02.004).

Expression Cassette for *S. Pombe*

Amplification of the promoter adh1 from genomic DNA of wild *S. pombe*

BS25 and BS26' (reverse)

Assembling the promoter adh1 (PCR product) and the ORF (pGLY02.001)

BS25 (forward) and BS20 (reverse)

The PCR amplification was extracted and purified from agarose gel with the Qiagen kit and was introduced into a vector TOPO2.1. Competent bacteria (TOP10, Invitrogen) were transformed with this vector. The transformation was checked by PCR and the insertion of the PCR amplification into the vector by sequencing (pGLY02.009).

Assembling the product promoter-ORF (pGLY02.009) with ORF-CYC1 (PCR product) BS25 (forward) and BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY02.011).

Amplification of the cassette (pGLY02.011) with flanking regions homologous to URA3 BS76 (forward) and BS77 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing.

3.3 Step 3: Transformation of the Yeasts

Preparation of competent yeasts:

S. Cerevisiae Adèle

Procedure: Sow 500 ml of yeasts at OD=0.1 and incubate them at 30° C. until 5.5<OD<6.5.

Centrifuge the cells at 1500 g for 5 min at 4° C. and re-suspend them in 500 mL of cold sterile water.

Centrifuge the cells and re-suspend them in 250 mL of cold sterile water.

Centrifuge the cells and re-suspend them in 20 mL of 1M sorbitol. Centrifuge the cells and re-suspend them in 1 mL of 1M sorbitol. Form 80 µL aliquots and store them at −80° C.

S. Pombe Edgar

Procedure: Sow 200 mL of yeasts at OD=0.1 and incubate them at 30° C. until OD=1.5.

Centrifuge at 3,000 rpm for 5 min at 20° C. Wash the cells in cold sterile water and centrifugate, wash a second time with 1 m sorbitol. Incubate for 15 min by adding DTT in order to reach a final 25 mM (in order to increase electrocompetence). Take up again as a final suspension in cold 1M sorbitol (density 1-5.10$^9$ cells/mL: about 5 mL). Form 40 µL aliquots and store about 10 vials at −80° C.

Transformation of the yeasts by electroporation:

For each expression cassette, the DNA used for transforming the yeasts either stems from a digestion of the mentioned plasmid with selected restriction enzymes, or directly from the obtained PCR product, purified after complete assembling.

S. cerevisiae cassette: pGLY02.004 is digested by the restriction enzymes BamHI and SmaI.

The competent yeasts are transformed with 1 µg of DNA: incubate for 5 min in ice. Give a pulse with V=1,500 V. Immediately add 1 mL of ice-cold sterile 1M sorbitol and transfer the cells with a Pasteur pipette into an Eppendorf tube and then let them relax for at least 1 hour in the Infors device at 30° C. Spread the yeasts on a dish of selection media (YPD containing 10 mM 5-fluorouracil, 5-FU). The transformants appear within 4-6 days.

S. pombe cassette: the competent yeasts are transformed with 100 ng of DNA (PCR product): incubate for 5 min in ice. The cells and the DNA are transferred into an electroporation tank. Give a pulse at V=1,500V and immediately add 0.9 mL of cold 1M sorbitol. The cells are spread as rapidly as possible on the suitable medium (YPD containing 10 mM 5-FU). The transformants appear within 4-6 days.

Example 4

Amélie and Emma strains+expression cassette for human N-acetyl-glucosaminyl transferase I 4.1 Step 1: Obtaining ORF PCR from a commercial plasmid Biovalley (Human ORF clone V1.1)

Program:

| |
|---|
| 5 minutes at 94° C. |
| 30 cycles: 60 s at 94° C. |
| 60 s at 56° C. |
| 2 min at 72° C. |
| 5 minutes at 72° C. |

Amplification of a 1,327 by fragment without the cytoplasmic portion of the enzyme. It will be replaced with the cytoplasmic portion of Mnn9 for Golgian localization of the protein.

Mnn9 cytoplasmic region: PCR from genomic DNA of wild S. cerevisiae

| |
|---|
| 8 minutes at 95° C. |
| 30 cycles: 20 s at 94° C. |
| 30 s at 58° C. |
| 1 min at 72° C. |
| 10 minutes at 72° C. |

Amplification of a 51 by fragment (cytoplasmic portion of mnn9).

(SEQ ID No 13)
Atgtcactttctcttgtatcgtaccgcctaagaaagaacccgtggttaac

From These Two PCR Amplifications:
Obtaining a Single Fragment (SEQ ID No 2)
Atgtcactttctcttgtatcgtaccgcctaagaaagaacccgtgggttaa
cgcagggcttgtgctgtggggcgctatcctcttt gtggcctggaatgccctgctgctcctcttcttctggacgcgcccagcacc
tggcaggccaccctcagtcagcgctctcgatgg cgacccgccagcctcacccgggaagtgattcgcctggcccaagacgccg
aggtggagctggagcggcagcgtgggctg ctgcagcagatcggggatgccctgtcgagccagcggggagggtgcccac
cgcggcccctcccgcccagccgcgtgtgc ctgtgaccccgcgccggcggtgattcccatcctggtcatcgcctgtgac
cgcagcactgttcggcgctgcctggacaagctg ctgcattatcggccctcggctgagctcttccccatcatcgttagccagga
ctgcgggcacgaggagacggcccaggccatcg cctcctacggcagcgcggtcacgcacatccggcagcccgacctgagcagc
attgcggtgccgccggaccaccgcaagttc cagggctactacaagatcgcgcgccactaccgctgggcgctgggccaggt
cttccggcagtttcgcttcccgcggccgtgg tggtggaggatgacctggaggtggccccggacttcttcgagtactttcgg
gccacctatccgctgctgaaggccgaccctcc ctgtggtgcgtctcggcctggaatgacaacggcaaggagcagatggtgga
cgccagcaggcctgagctgctctaccgcacc -continued
```
gactttttccctggcctgggctggctgctgttggccgagctctgggctga
gctggagcccaagtggccaaaggccttctggga cgactggatgcggcggccggagcagcggcaggggcgggcctgcatacgcc
ctgagatctcaagaacgatgacctttggcc gcaagggtgtgagccacgggcagttctttgaccagcacctcaagtttatc
aagctgaaccagcagtttgtgcacttcacccagc tggacctgtcttacctgcagcgggaggcctatgaccgagatttcctcgcc
cgcgtctacggtgctccccagctgcaggtggag aaagtgaggaccaatgaccggaaggagctgggggaggtgcgggtgcagta
tacgggcagggacagcttcaaggctttcgc caaggctctgggtgtcatggatgaccttaagtcggggggttccgagagctg
gctaccggggtattgtcaccttccagttccggg gccgccgtgtccacctggcgcccccactgacgtgggagggctatgatcct
agctggaattagcacctgcctgtccttc
```

The amplification product of the assembling PCR was purified from agarose gel with the QIAGEN kit and was introduced into a vector TOPO2.1. Competent bacteria (TOP10, Invitrogen) were transformed with this vector. The transformation was checked by PCR and the insertion of the PCR amplification into the vector by sequencing (pGLY03.001).

4.2 Step2: Assembling the Expression Cassette

Expression Cassette for *S. Cerevisiae*

The integration of the expression cassette of the GlcNAc transferase I for the yeast *S. cerevisiae* will be localized in the auxotrophy marker ADE2. Invalidation of this gene induces a change in the color of the yeasts which become red and also auxotrophy for adenine.

of the promoter adh 1 from genomic DNA of *S. cerevisiae*
BS29 (forward) and BS30 (reverse)
Assembling the promoter adh 1 (PCR product) and the ORF (pGLY03.001):
BS29 (forward) and BS59

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification in the vector by sequencing (pGLY03.002).
Assembling of the ORF (pGLY03.001) with the terminator CYC1 (PCR product):
CA005 (forward)
BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY03.011).
Assembling the promoter-ORF (pGLY03.002) and the ORF-terminator (PCR product) with the extensions homologous to ADE2:
BS67 (forward) and BS68 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY03.010).

Expression Cassette for *S. Pombe*

The integration of the expression cassette of the GlcNAc transferase I for the yeast *S. pombe* will be localized in the auxotrophy marker ADE1. Invalidation of this gene induces a change in the color of the yeasts which become red and also auxotrophy for adenine.

Amplification of the promoter hCMV from the plasmid pCDNA 3.1
BS62 (forward) and BS58 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY03.004).
Assembling hCMV-ORF (pGLY03.004) with the terminator CYC1 (PCR product) BS62 (forward) and BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY03.005).
Assembling the expression cassette (pGLY03.005) with the extensions homologous to ADD:
BS69 (forward) and BS70 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY03.007).

4.3 Step 3: Transformation of the Yeasts
Preparation of Competent Yeasts:

The Amélie and Emma strains were prepared as indicated above in order to make them competent.
Electroporation of the Yeasts *S. Cerevisiae* and *S. Pombe*
Procedure:
20 µg of plasmids containing the expression cassette for *S. cerevisiae* and *S. pombe* were digested by the restriction enzyme EcoRI. The linearized cassette was introduced in the yeasts Amélie and Emma by electroporation. The yeasts are selected on an YNB medium containing the required amino acids.

Example 5

Agathe and Egée strains+expression cassette for the UDP-GlcNAc transporter 5.1 Step 1: Obtaining the ORF
Program:

| |
|---|
| 3 minutes at 94° C. |
| 30 cycles:  20 s at 94° C. |
|             30 s at 58° C. |
|             2 min at 72° C. |
| 10 minutes at 72° C. |

Amplification of a 916 by Fragment (SEQ ID No 3)
```
atgttcgccaacctaaaatacgtttccctgggaattttggtcttttcagac taccagtttggttctaacaatgcgttattccagaact ttaaaagaagaaggacctcgttatctatcttctacagcagtggttgttgc
```

-continued

```
tgaacttttgaagataatggcctgcattttattggtcta caaagacagcaaatgtagtctaagagcactgaatcgagtactacatgatg aaattcttaataaacctatggaaacacttaaactt gctattccatcagggatctatactcttcagaataatttactgtatgtggc actatcaaatctagatgcagctacttatcaggtcacgt atcagttgaaaattcttacaacagcattattttctgtgtctatgcttagt aaaaaattgggtgtataccagtggctgtccctagtaattt tgatgacaggagttgcttttgtacagtggccctcagattctcagcttgat tctaaggaactttcagctggttctcaatttgtaggact catggcagttctcacagcatgtttttcaagtggctttgctggggtttact ttgagaaaatcttaaaagaaacaaaacaatcagtgtg gataagaaatattcagcttggtttctttggaagtatatttggattaatgg gtgtatacatttatgatggagaactggtatcaaagaatg gattttttcagggatataaccgactgacctggatagtagttgttcttcag gcacttggaggccttgtaatagctgctgttattaagtat gcagataatattttaaaaggatttgcaacctctttatcgataatattatc aacattgatctcctatttttggcttcaagattttgtgccaa ccagtgtctttttccttggagccatccttgtaa
```

The PCR amplification was extracted and purified from agarose gel with the QIAGEN kit and was introduced into a vector TOPO2.1. Competent bacteria (TOP10, Invitrogen) were transformed with this vector. The transformation was checked by PCR and the insertion of the PCR amplification into the vector by sequencing (pGLY04.001).

5.2 Step 2: Assembling the Expression Cassette
Cassette for S. Cerevisiae and for S. Pombe The integration of the expression cassette of the UDP-GlcNAc transporter will be localized in the auxotrophy marker LYS2 for both strains S. cerevisiae and S. pombe. Invalidation of this gene induces resistance to a toxic agent, alpha-aminoadipic acid. The yeasts modified by this cassette will therefore become resistant to this drug but also auxotrophic for lysine.

Amplification of the promoter PGK from the plasmid pFL61
BS95 (forward) and BS96 (reverse)
Assembling the ORF (pGLY04.001) with the terminator CYC1 (PCR product)
CA017 (forward) and BS41 (reverse)

The PCR amplification was extracted and purified from agarose gel with the Qiagen kit and was introduced into a vector TOPO2.1. Competent bacteria (TOP10, Invitrogen) were transformed with this vector. The transformation was checked by PCR and the insertion of the PCR amplification into the vector by sequencing (pGLY04.002).

Assembling the promoter PGK (PCR product) with the ORF-terminator CYC1 fragment (pGLY04.002):
BS95 (forward) and BS41 (reverse)
Assembling the expression cassette with the extensions homologous to LYS2
S. cerevisiae:
BS97 (forward) and BS98 (reverse)
S. Pombe
BS99 (forward)
BS100 (reverse)

The PCR amplifications were extracted and purified from agarose gel with the Qiagen kit and were introduced into a vector pTarget. Competent bacteria (JM109, Promega) were transformed with this vector. The transformation was checked by PCR and the insertion of the PCR amplification into the vector by sequencing (pGLY04.006) for the S. cerevisiae cassette and pGLy04.005 for the S. pombe cassette).

5.3 Step 3: Modification of the Yeasts
Preparation of Competent Yeasts:
The Agathe and Egée strains were prepared as indicated above in order to make them competent
Electroporation of the Yeasts:
20 µg of the plasmids containing the expression cassettes for S. cerevisiae, S. pombe were digested by the restriction enzyme EcoRI. The linearized cassette was introduced into the yeasts Agathe and Egée by electroporation. The yeasts are selected on an YNB medium containing the required amino acids and alpha-aminoadipic acid.

Example 6

Arielle and Erika Strains+Expression Cassette for α-mannosidase II 6.1 Step 1: Obtaining the oRF
PCR from cDNA of mouse liver
Program:

| |
|---|
| 3 minutes at 94° C. |
| 35 cycles: 20 s at 94° C. |
| 30 s at 58° C. |
| 4 min at 72° C. |
| 10 minutes at 72° C. |

Amplification of a 3,453 by fragment

```
                                            (SEQ ID No 4)
atgaagttaagtcgccagttcaccgtgtttggcagcgcgatcttctgcgt cgtaatcttctcactctacctgatgctggacagg ggtcacttggactaccctcggggcccgcgccaggagggctcctttccgca gggccagctttcaatattgcaagaaaagattga ccatttggagcgtttgctcgctgagaacaacgagatcatctcaaatatca gagactcagtcatcaacctgagcgagtctgtgga ggacggcccgcgggggtcaccaggcaacgccagccaaggctccatccacc tccactcgccacagttggccctgcaggctg accccagagactgtttgtttgcttcacagagtgggagtcagccccggat gtgcagatgttggatgtttacgatctgattccttttg ataatccagatggtggagtttggaagcaaggatttgacattaagtatgaa gcggatgagtgggaccatgagcccctgcaagtg tttgtggtgcctcactcccataatgacccaggttggttgaagactttcaa tgactactttagagacaagactcagtatattttaataa catggtcctaaagctgaaagaagactcaagcaggaagtttatgtggtctg agatctcttaccttgcaaaatggtgggatattatag atattccgaagaaggaagctgttaaaagtttactacagaatggtcagctg
```

```
gaaattgtgaccggtggctgggttatgcctgatga
agccactccacattattttgccttaattgaccaactaattgaagggcacc
aatggctggaaaaaaatctaggagtgaaacctcga
tcgggctgggccatagatccctttggtcattcacccacaatggcttatct
tctaaagcgtgctggattttcacacatgctcatccag
agagtccattatgcaatcaaaaaacacttctctttgcataaaacgctgga
gttttctggagacagaattgggatcttggatctgct
acagacattttgtgccatatgatgccttctacagctacgacatccctca
cacctgtgggcctgatcctaaaatatgctgccagttt
gattttaaacggcttcctggaggcagatatggttgtccctggggagttcc
cccagaagcaatatctcctggaaatgtccaaagc
agggctcagatgctattggatcagtaccggaaaaagtcaaaacttttccg
cactaaagttctgctggctccactgggagacgac
tttcggttcagtgaatacacagagtgggatctgcagtgcaggaactacga
gcaactgttcagttacatgaactcgcagcctcatc
tgaaagtgaagatccagtttggaaccttgtcagattatttcgacgcattg
gagaaagcggtggcagccgag 6.3 Step 3: Modification of the Yeasts Preparation of competent yeasts:

The Arielle and Erika strains were prepared as indicated above in order to make them competent Electroporation of the Yeasts Procedure: 20 µg of the plasmids containing the expression cassette for *S. cerevisiae* and *S. pombe* were digested by the restriction enzyme EcoRI. The linearized cassette was introduced into the yeasts Arielle and Erika by electroporation. The yeasts are selected on an YNB medium containing the required amino acids as well as tri-fluoroleucine (TFL) of *S. cerevisiae* and *S. pombe*

Example 7

Anaïs and Enrique Strains+Expression Cassette of N-acety-glucosaminyl transferase II 6.1 Step 1: Obtaining the OR PCR from complementary DNA of human fibroblasts—Use of Taq polymerase Isis™ (Q-Biogene)

Program:

3 minutes at 94° C.
30 cycles: 30 s at 94° C.
30 s at 58° C.
1.30 min at 68° C.

Amplification of a 1,344 by fragment (SEQ ID No 5)
atgaggttccgcatctacaaacggaaggtgctaatcctgacgctcgtggt ggccgcctgcggcttcgtcctctggagcagca atgggcgacaaaggaagaacgaggccctcgccccaccgttgctggacgcc gaacccgcgcgggtgccggcggccgcg gtggggaccaccctctgtggctgtgggcatccgcagggtctccaacgtg tcggcggcttccctggtcccggcggtcccca gcccgaggcggacaacctgacgctgcggtaccggtccctggtgtaccagc tgaactttgatcagaccctgaggaatgtagat aaggctggcacctgggcccccgggagctggtgctggtggtccaggtgca -continued taaccggcccgaatacctcagactgctgctg gactcacttcgaaaagcccagggaattgacaacgtcctcgtcatctttag ccatgacttctggtcgaccgagatcaatcagctga tcgccggggtgaatttctgtccggttctgcaggtgttctttcctttcagc attcagttgtaccctaacgagtttccaggtagtgaccc tagagattgtcccagagacctgccgaagaatgccgctttgaaattgggt gcatcaatgctgagtatcccgactccttcggcca ttatagagaggccaaattctcccagaccaaacatcactggtggtggaagc -continued tgcattttgtgtgggaaagagtgaaaattcttcga gattatgctggccttatactttcctagaagaggatcactacttagcccc agacttttaccatgtcttcaaaaagatgtggaaactg aagcagcaagagtgccctgaatgtgatgttctctccctggggacctatag tgccagtcgcagtttctatggcatggctgacaag gtagatgtgaaaacttggaaatccacagagcacaatatgggtctagcctt gacccggaatgcctatcagaagctgatcgagtg cacagacacttctgtacttatgatgattataactgggactggactcttc aatacttgactgtatcttgtcttccaaaattctggaaag tgctggttcctcaaattcctaggatctttcatgctggagactgtggtatg catcacaagaaaacctgtagaccatccactcagagt gcccaaattgagtcactcttaaataataacaaacaatacatgtttccaga aactctaactatcagtgaaaagtttactgtggtagcc atttccccacctagaaaaaatggagggtggggagatattagggaccatga actctgtaaaagttatagaagactgcagtga

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY08.002).

Cytoplasmic region of mmn9: PCR from genomic DNA of wild *S. cerevisiae*

8 minutes at 94° C.
30 cycles: 20 s at 94° C.
30 s at 65° C.
1 min at 72° C.
10 minutes at 72° C.

Amplification of a 51 by fragment (cytoplasmic portion of mmn9)+homology to

GNTII <u>Atgtcactttctcttgtatcgt</u>accgcctaag<u>aaagaaccgtgggttaacaggttccgcatctac</u>

Assembling Mnn9 (PCR product) and the ORF (pGLY08.002) with Taq Platinium

CA005 (forward) and CD005 (reverse)

Program:

2 minutes at 95° C.
30 cycles: 45 s at 95° C.
45 s at 54° C.
2 min at 72° C.
10 minutes at 72° C.

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY08.007).

7.2 Step 2: Assembling Expression Cassette for *S. Cerevisiae* and *S. Pombe* Strains The integration of the expression cassette of the GlcNAc-transferase II will be inserted into the Lem3 marker for *S. cerevisiae* and TRP1 marker for *S. pombe*. Invalidation of the gene Lem3 induces a resistance to a toxic agent, miltefosine. The yeasts modified by this cassette will therefore become resistant to this drug. Invalidation of the gene TRP1 induces a resistance to a toxic agent, 5-fluoro-anthranilic acid. The yeasts modified by this cassette will therefore become resistant to this drug but also auxotrophic for tryptophan.

Amplification of the promoter PMA1

```
CD001 (forward)
aagcttcctgaaacggag

CD008 (reverse)
acgatacaagagaaagtgacatattgatattgtttgataattaaat
```

PCR from genomic DNA of *S. cerevisiae*

Program:

| |
|---|
| 2 minutes at 95° C. |
| 30 cycles: 45 s at 95° C. |
| 45 s at 54° C. |
| 2 min at 72° C. |
| 5 minutes at 72° C. |

Assembling the promoter PMA1 (PCR product) with Mnn9-homology ORF (pGLY08.007) with Taq Expand (Roche)

```
CD007    cgtttgtagatgcggaacctgttaacccacgggttctttt
CD001    aagcttcctgaaacggag
```

| |
|---|
| 2 minutes at 94° C. |
| 30 cycles: 45 s at 94° C. |
| 45 s at 55° C. |
| 1.15 min at 68° C. |
| 5 minutes at 68° C. |

The PCR amplification was purified by the phenol/chloroform method and introduced into the vector TOPO2.1 (Invitrogen). Competent bacteria (TOP10, Invitrogen) were transformed with this vector. The transformation was checked by PCR and the insertion of the PCR amplification into the vector by sequencing (pGLY08.005).

Assembling Mnn9-ORF (pGLY08.007) with the terminator CYC1 (PCR product) with Taq polymerase Phusion™ (Ozyme)

Program

| |
|---|
| 2 minutes at 98° C. |
| 3 cycles: 10 s at 98° C. |
| 30 s at 52° C. |
| 40 s at 72° C. | addition of the primers and then

| |
|---|
| 30 cycles 10 s at 98° C. |
| 30 s at 61° C. |
| 40 s at 72° C. |
| 5 min at 72° C. |

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY08.04).

Assembling the promoter PMA1-Mnn9 (pGLY08.009) with Mnn9-ORF-terminator CYC1 (PCR product) with the ends homologous to the marker Lem3 for *S. cerevisiae* with Taq polymerase Phusion™ (Ozyme)

```
CB053: Atggtaaatttcgatttgggccaagttggtgaagtattccaagcttcctgaaacggag (forward)

CB070: Ttctaccgccgaagagccaaaacgttaataatatcaatggcagcttgcaaattaaagc (reverse)
```

Program

| |
|---|
| 2 minutes at 98° C. |
| 3 cycles: 10 s at 98° C. |
| 30 s at 52° C. |
| 4 min at 72° C. | addition of the primers and then

| |
|---|
| 30 cycles 10 s at 98° C. |
| 30 s at 61° C. |
| 1 min at 72° C. |
| 5 min at 72° C. |

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY08).

Assembling the ends homologous to the marker TRP1 for *S. pombe* from pGLY08.012

```
CD009 (forward)  taaagttgattccgctggtgaaatcatacatggaaaagtttaagcttcctgaaacggag
CD010 (reverse)  atgtgaaatttccttggccacggacaagtccacttttcgtttggcagcttgcaaattaaagc
```

7.3 Step 3: Modification of the Yeasts
Preparation of competent yeasts:
The Anaïs and Enrique strains were prepared as indicated above in order to make them competent.
Electroporation of the yeasts
Procedure: 20 μg of the plasmids containing the expression cassette for *S. cerevisiae* and *S. pombe* were digested by the restriction enzyme EcoRI. The linearized cassette was introduced into the yeasts Anaïs and Enrique by electroporation. The yeasts are then spread over a gelosed YPD medium containing the required selection drug.

Example 8

Alice and Elga Strains+Expression Cassette of Galactosyl Transferase I 8.1 Step 1: Obtaining the ORF Without the Human Localization Sequence
PCR from cDNA of human lymphoblasts
CD025 (forward) CD026 (reverse)

| | |
|---|---|
| 2 minutes at 94° C. | |
| 30 cycles: | 45 s at 94° C. |
| | 45 s at 58° C. |
| | 1.15 min at 72° C. |
| 5 minutes at 72° C. | |

Amplification of a 1,047 by fragment (SEQ ID No 6)
ccccaactggtcggagtctccacaccgctgcagggcggctcgaacagtgc cgccgccatcgggcagtcctccggggagc tccggaccggaggggcccggccgccgcctcctctaggcgcctcctcccag ccgcgcccgggtggcgactccagcccagt cgtggattctggccctggcccgctagcaacttgacctcggtcccagtgc cccacaccaccgcactgtcgctgcccgcctgc cctgaggagtccccgctgcttgtgggcccatgctgattgagtttaacat gcctgtggacctggagctcgtggcaaagcagaa cccaaatgtgaagatgggcggccgctatgccccagggactgcgtctctc ctcacaaggtggccatcatcattccattccgca accggcaggagcacctcaagtactggctatattatttgcacccagtcctg cagcgccagcagctggactatggcatctatgttat caaccaggcgggagacactatattcaatcgtgctaagctcctcaatgttg gctttcaagaagccttgaaggactatgactacacc tgctttgtgtttagtgacgtggacctcattccaatgaatgaccataatgc gtacaggtgtttttcacagccacggcacatttccgttg -continued
caatggataagtttggattcagcctaccttatgttcagtattttggaggt gtctctgctctaagtaaacaacagtttctaaccatcaat ggatttcctaataattattggggctggggaggagaagatgatgacatttt taacagattagtttttagaggcatgtctatatctcgcc caaatgctgtggtcgggaggtgtcgcatgatccgccactcaagagacaag aaaaatgaacccaatcctcagaggtttgaccg aattgcacacacaaaggagacaatgctctctgatggtttgaactcactca cctaccaggtgctggatgtacagagatacccattg tatacccaaatcac agtggacatcgggacaccgacctag.

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY11.003).

Mnt1 localization: PCR from gDNA of *S. cerevisiae*

| | |
|---|---|
| 3 minutes at 94° C. | |
| 30 cycles: | 20 s at 94° C. |
| | 30 s at 58° C. |
| | 45 s at 72° C. |
| 10 minutes at 72° C. | |

Amplification of a 246 by fragment—SEQ ID NO 14 atggccctctttctcagtaagagactgttgagatttaccgtcattgcagg tgcggttattgttctcctcctaacattgaattccaac agtagaactcagcaatatattccgagttccatctccgctgcatttgattt tacctcaggatctatatcccctgaacaacaagtcatct ctgaggaaatgatgctaaaaaattagagcaaagtgctctgaattcagag gcaagcgaagactccgaagcc

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing.

8.2: Step 2: Assembling Expression Cassettes for the *S. Cerevisiae* and *S. Pombe* Strains The integration of the expression cassettes of Galactosyl transferase I will be localized in the marker TRP1 for *S. cerevisiae* Alice. Invalidation of this gene induces resistance to a toxic agent, fluoroanthranilic acid. The yeasts modified by this cassette will therefore become resistant to this drug. The integration of the expression cassette of Galactosyl transferase I will be localized in the marker Met17 for *S. cerevisiae* Ashley.

Amplification of the promoter CaMV from the plasmid pMDC:
CD035 (forward)
CD037 (reverse)
Program 2 minutes at 94° C.
30 cycles: 45 s at 94° C.
45 s at 65° C.
2 min 30 s at 72° C.
5 minutes at 72° C.

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY11.001).

CD063 (forward) agatgccagaaacaaagcttgttgcaggtggtgctgctcatgcctgcaggtcaacatggt

CD064 (reverse) gtgtcgacgatcttagaagagtccaaaggtttgactggatgcagcttgcaaattaaagcc

Assembling the promoter CaMV (pGLY11.001) with the Mnt1 localization sequence (PCR product):
CD035 (forward) and CD028 (reverse)
Program:

2 minutes at 94° C.
30 cycles: 45 s at 94° C.
45 s at 59° C.
1 min 15 s at 72° C.
3 minutes at 72° C.

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY11.002).
Assembling the promoter CaMV-Mnt1 localization (pGLY011.002) with the ORF (PCR product).
CD035 (forward)
CD029 (reverse)
Program:

2 minutes at 94° C.
30 cycles: 45 s at 94° C.
45 s at 56° C.
2 min 30 s at 72° C.
3 minutes at 72° C.

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY011.004).
Assembling the promoter CaMV-localization Mnt1-ORF (pGLY011.004) with the terminator CYC1 (PCR product) with Taq Expand (Roche)
CD035 (forward) BS41 (reverse)

Program:

3 minutes at 95° C.
30 cycles: 30 s at 95° C.
30 s at 57° C.
2 min 30 s at 68° C.
10 minutes at 68° C.

The PCR amplification was purified by the phenol/chloroform method and introduced into the vector pTarget (Promega). Competent bacteria (JM109, Promega) were transformed with this vector. The transformation was checked by PCR and the insertion of the PCR amplification into the vector by sequencing (pGLY011.005).
Assembling the integration cassette for S. cerevisiae with Taq Expand (Roche)

Program 3 minutes at 95° C.
30 cycles: 30 s at 95° C.
30 s at 57° C.
2 min 30 s at 68° C.
10 minutes at 68° C.

The PCR amplification was purified by the phenol/chloroform method and introduced into the vector TOPO 2.1 (Invitrogen). Competent bacteria (TOP10 Invitrogen) were transformed with this vector. The transformation was checked by PCR and the insertion of the PCR amplification into the vector by sequencing (pGLY011.008).
For S. pombe, integration into the sequence PET6
Use of Taq Expand (Roche)
CD038 (forward) and CD039 (reverse)
The PCR products were introduced into a vector TOPO-XL. Competent bacteria (TOP10, Invitrogen) were transformed with this vector. The transformation was checked by PCR and the insertion of PCR amplification into the vector by sequencing (pGLY11.006 for S. pombe and pGLY11.007 for S. cerevisiae).

8.3 Step 3: Modification of the Yeasts

Preparation of competent yeasts:

The Alice and Elga strains were prepared as indicated above in order to make them competent.

Electroporation of the yeasts

Procedure: 20 µg of the plasmids containing the expression cassettes for S. cerevisiae and S. pombe were digested by restriction enzymes KpnI and XhoI. The linearized cassette was introduced into the yeasts Alice and Elga by electroporation. The yeasts were then spread on a gelosed YPD medium containing the required selection.

Example 9

Strains Anaïs and Enrique+Expression Cassettes for Fucosylation (α1,6-Fucosyl Transferase FUT8 and GDP-Fucose Transporter)

9.1 Expression Cassette of FUT8
9.1.1 Step 1: Obtaining the ORF
PCR from cDNA of human pancreas and lungs
Program:

| |
|---|
| 3 minutes at 94° C. |
| 35 cycles: 20 s at 94° C. |
| 30 s at 58° C. |
| 2 min at 72° C. |
| 10 minutes at 72° C. |

Amplification of a 1,801 by fragment (SEQ ID No 7)
caggactccagggaagtgagttgaaaatctgaaaatgcggccatggactg gttcctggcgttggattatgctcattcttttttgcc tgggggaccttgctgttttatataggtggtcacttggtacgagataatga ccatcctgatcactctagccgagaactgtccaagat tctggcaaagcttgaacgcttaaaacagcagaatgaagacttgaggcgaa tggccgaatctctccggataccagaaggccct attgatcaggggccagctataggaagagtacgcgttttagaagagcagct tgttaaggccaaagaacagattgaaaattacaa gaaacagaccagaaatggtctggggaaggatcatgaaatcctgaggagga ggattgaaaatggagctaaagagctctggttt ttcctacagagtgaattgaagaaattaaagaacttagaaggaaatgaact ccaaagacatgcagatgaatttcttttggatttagg acatcatgaaaggtctataatgacggatctatactacctcagtcagacag atggagcaggtgattggcgggaaaaagaggcc aaagatctgacagaactggttcagcggagaataacatatcttcagaatcc caaggactgcagcaaagccaaaaagctggtgt gtaatatcaacaaaggctgtggctatggctgtcagctccatcatgtggtc tactgcttcatgattgcatatggcacccagcgaac actcatcttggaatctcagaattggcgctatgctactggtggatgggaga ctgtatttaggcctgtaagtgagacatgcacagac agatctggcatctccactggacactggtcaggtgaagtgaaggacaaaaa tgttcaagtggtcgagcttcccattgtagacagt cttcatccccgtcctccatatttaccctggctgtaccagaagacctcgc agatcgacttgtacgagtgcatggtgaccctgcagt gtggtgggtgtctcagtttgtcaaatacttgatccgcccacagccttggc tagaaaaagaaatagaagaagccaccaagaagc ttggcttcaaacatccagttattggagtccatgtcagacgcacagacaaa gtgggaacagaagctgccttccatcccattgaag agtacatggtgcatgttgaagaacattttcagcttcttgcacgcagaatg caagtggacaaaaaaagagtgtatttggccacaga tgaccccttctttattaaaggaggcaaaaacaaagtaccccaattatgaat ttattagtgataactctatttcctggtcagctggactg cacaatcgatacacagaaaattcacttcgtggagtgatcctggatataca ttttctctctcaggcagacttcctagtgtgtacttttttc atcccaggtctgtcgagttgcttatgaaattatgcaaacactacatcctg atgcctctgcaaacttccattctttagatgacatctact attttgggggccagaatgcccacaatcaaattgccatttatgctcaccaa ccccgaactgcagatgaaattcccatggaacctg gagatatcattggtgtggctggaaatcattgggatggctattctaaaggt gtcaacaggaaattgggaaggacgggcctatatc cctcctacaaagttcgagagaagatagaaacggtcaagtaccccacatat cctgaggctgagaaataaagctcagatggaag agataaacgaccaaact cagttcga

The PCR amplification (1,801 by from cDNA of human lungs and pancreas) was extracted and purified from agarose gel with the QBIOgene kit and was introduced into a vector TOPO2.1. Competent bacteria (TOP10, Invitrogen) were transformed with this vector. The transformation was checked by PCR and the insertion of the PCR amplification into the vector by sequencing.

9.1.2 Step2: Assembling the Expression Cassette for *S. Cerevisiae*

Amplification of the promoter mnt1 from genomic DNA of *S. pombe*
BS86 (forward) and BS84 (reverse)
Assembling the promoter mnt1 (PCR product) with the ORF (pGLY06.001)
BS86 (forward) and BS88 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY06.003).

Assembling the ORF (pGLY06.001) with the terminator CYC1 (PCR product)
CA011 (forward) and BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY06.002).

Assembling nmt1-ORF (pGLY06.003) with ORF-terminator CYC1 (PCR product)
BS86 (forward) and BS41 (reverse)
Assembling the ends for integration into auxotrophy markers of yeasts:

9.1.2.1 *S. Cerevisiae*

The integration of the expression cassette of FUT8 was localized in the marker CAN1 for *S. cerevisiae* strain. Invalidation of the gene CAN1 induces auxotrophy for canavanine.
BS147 (forward) and BS148 (reverse)

The PCR amplifications were extracted and purified from agarose gel with the Qiagen kit and were introduced into a vector pTarget. Competent bacteria (JM109, Promega) were transformed with this vector. The transformation was checked by PCR and the insertion of the PCR amplification into the vector by sequencing (pGLY06.005).

9.1.2.2 *S. Pombe*

The expression cassette for fucosyl transferase 8 was produced in tandem with a cassette for resistance to an antibiotic, phleomycin. This double cassette is inserted in a simple auxotrophy marker HIS5. Insertion of this cassette into this locus will induce resistance to phleomycin as well as auxotrophy for histidine.

The expression cassette of FUT8 obtained previously is assembled with an expression cassette of phleomycin comprising the promoter of SV40, the ORF of the resistance to phleomycin as well as the terminator TEF. These tandem cassettes are inserted into the marker HIS5.

9.1.3 Step 3: Modification of the Yeasts

Preparation of competent yeasts:

The Anaïs and Enrique strains were prepared as indicated above in order to make them competent.

Electroporation of the yeasts

Procedure: 20 μg of plasmids containing the expression cassette for *S. cerevisiae* and *S. pombe* were digested by the restriction enzyme EcoRI. The linearized cassette was introduced into the yeasts Anaïs and Enrique by electroporation. The yeasts are spread with a limiting dilution on a gelosed YPD medium, the deleted markers do not impart resistance to a drug. Once the clones have been released, replicates on a minimum medium are established in order to select the clones which can no longer grow without the required amino acid.

9.2 Expression Cassette of the GDP-Fucose Transporter 9.2.1 Obtaining the ORF

PCR from cDNA of human lungs

Program:

---
3 minutes at 94° C.
35 cycles: 20 s at 94° C.
30 s at 58° C.
2 min at 72° C.
10 minutes at 72° C.
---

Amplification of a 1,136 by fragment (SEQ ID No 8)
tgacccagctcctctgctaccatgaatagggcccctctgaagcggtccag gatcctgcacatggcgctgaccggggcctca gacccctctgcagaggcagaggccaacggggagaagccctttctgctgcg ggcattgcagatcgcgctggtggtctccctct actgggtcacctccatctccatggtgttccttaataagtacctgctggac agccctccctgcggctggacaccccatcttcgt caccttctaccagtgcctggtgaccacgctgctgtgcaaaggcctcagcg ctctggccgcctgctgccctggtgccgtggact tccccagcttgcgcctggacctcagggtggcccgcagcgtcctgccctg tcggtggtcttcatcggcatgatcaccttcaata acctctgcctcaagtacgtcggtgtggccttctacaatgtgggccgctca ctcaccaccgtcttcaacgtgctgctctcctacctg ctgctcaagcagaccacctccttctatgccctgctcacctgcggtatcat catcggggcttctggcttggtgtggaccaggag ggggcagaaggcaccctgtcgtggctgggcaccgtcttcggcgtgctggc tagcctctgtgtctcgctcaacgccatctacac cacgaaggtgctcccggcggtggacggcagcatctggcgcctgactttct acaacaacgtcaacgcctgcatcctcttcctgc ccctgctcctgctgctcggggagcttcaggccctgcgtgactttgcccag ctgggcagtgcccacttctgggggatgatgacg ctgggcggcctgtttggctttgccatcggctacgtgacaggactgcagat caagttcaccagtccgctgacccacaatgtgtcg ggcacggccaaggcctgtgcccagacagtgctggccgtgctctactacga ggagaccaagagcttcctctggtggacgagc aacatgatggtgctgggcggctcctccgcctacacctgggtcaggggctg ggagatgaagaagactccggaggagcccag ccccaaagacagcgagaag ag cgccatgggggtgtgagcaccacaggcaccctggat

The PCR amplification was extracted and purified from agarose gel with the QIAGEN kit and was introduced into a vector TOPO2.1. Competent bacteria (TOP10, Invitrogen) were transformed with this vector. The transformation was checked by PCR and the insertion of the PCR amplification into the vector by sequencing (pGLY07.001).

9.2.2 Step 2: Assembling the Expression Cassette for *S. Cerevisiae* and *S. Pombe*

Amplification of the promoter SV40 from pTarget:

BS109 (forward) and BS110 (reverse)

Assembling the ORF (pGLY07.001) with the terminator CYC1 (PCR product) CA013 (forward) and BS41 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY07.002).

9.2.2.1 *S. Cerevisiae*

The integration of the expression cassette of the GDP-fucose transporter will be localized in the auxotrophy marker TRP1 for the *S. cerevisiae* strain. Invalidation of the gene TRP1 induces resistance to a toxic agent, 5-fluoro-anthranilic acid. The yeasts modified by this cassette will therefore become resistant to this drug but also auxotrophic for tryptophan.

Assembling the promoter SV40 cassette (PCR product), the ORF (PCR product) and the terminator CYC1 (PCR product)

BS136 (forward) and BS137 (reverse)

The PCR amplification was extracted and purified from agarose gel with the Qiagen kit and was introduced into a vector pTarget. Competent bacteria (JM109, Promega) were transformed with this vector. The transformation was checked by PCR and the insertion of the PCR amplification into the vector by sequencing (pGLY07.003).

9.2.2.2 S. Pombe

The expression cassette for the GDP-fucose transporter was produced in tandem with a cassette for resistance to an antibiotic, hygromycin. This double cassette is inserted in a gene coding for a protein involved in the maturation of N-glycans of S. pombe, GMA12. Insertion of this cassette in this locus will induce resistance to hygromycin but also the deletion of the gene gma12.

The expression cassette of the GDP-fucose transporter obtained previously is assembled with an expression cassette of resistance to hygromycin comprising the promoter of SV40, the ORF of the resistance to hygromycin as well as the terminator TEF. These tandem cassettes are inserted into the marker gma12.

9.2.3 Step 3: Modification of the Yeasts

Preparation of competent yeasts:

The Apolline and Epiphanie strains were prepared as indicated above in order to make them competent.

Electroporation of the yeasts

Procedure: 20 μg of plasmids containing the expression cassettes for S. cerevisiae and S. pombe were digested by the restriction enzyme EcoRI. The linearized cassette was introduced into the yeasts Apolline and Epiphanie by electroporation. The S. cerevisiae yeasts are spread on an YPD medium containing 5-fluoro-anthranilic acid. The S. pombe yeasts are spread with limiting dilution on a gelosed YPD medium, the deleted marker not imparting resistance to a drug. Once the clones are released, replicates on a minimum medium are established in order to select the clones which cannot grow without the required amino acid.

Example 10

Athena and Etienne Strains+Expression Cassette of N-Acetylglucosaminyl-Transferase III

10.1 Obtaining the ORF

PCR from complementary DNA of murine brain

```
CB007 (forward)    Atgaagatgagacgctacaa
CB036 (reverse)    ctagccctccactgtatc
```

Program:

| | |
|---|---|
| 2 minutes at 94° C. | |
| 30 cycles: | 45 s at 94° C. |
| | 45 s at 56° C. |
| | 2 min at 72° C. |
| 5 minutes at 72° C. | |

Amplification of a by fragment without the cytoplasmic portion of the enzyme: it will be replaced with the cytoplasmic portion of Mnt1 for Golgian localization of the protein.

10.2 Expression Cassette Assembling for the S. Cerevisiae and S. Pombe Strains

10.2.1 Assembling for S. Cerevisiae

Amplification of the promoter nmt1

```
CB013: tatagtcgctttgttaaatcatatggccctctttctcagtaa
CB014: agcgaagactccgaagcccacttctttaagaccttatcc
```

Amplification of the terminator CYC1
Amplification of the expression cassette with the ends CAN1

```
CB030 (forward):    cagaaaatccgttccaagag
CB031 (reverse):    tgccacggtatttcaaagct
```

10.2.2 Assembling for S. Pombe

Expression cassette of GNTIII in tandem with a cassette for resistance to hygromycin. Insertion in GMA12.

10.3 Transformation of the Yeasts

Example 11

Deletion of Genes Involved in Hypermannosylation in S. Cerevisiae and S. Pombe

11.1 Step 1: Deletion of the Mnn1 Gene in the Yeasts Amélie, Arielle, Anaïs, Alice, Abel, Ashley, Athena, Azalée and Aurel

11.1.1 Construction and Insertion of a Cassette Containing a Gene for Resistance to Hygromycin into the Mnn1 Gene

11.1.1.1 Construction of the Expression Cassette

Amplification of the promoter CaMV with the Mnn1 5' end

```
CB39:
TTTATATTAAACCAAAGGTCTTTGAGATCGTGTACCATACTGCCTGCAGG
TCAACATG

CB40:
TTCTCGACAGACGTCGCGGTGAGTTCAGGCTTTTTACCCATCCGGGGATC
CTCTAGAGTC
```

Hygromycin-terminator TEF amplification with homology to the promoter CaMV and the Mnn1 3' end

```
CB41:
TTCATTTGGAGAGGACCTCGACTCTAGAGGATCCCCGGATGGGTAAAAAG
CCTGAACTC

CB42:
GGTGTTATCTTTATTAGCATGTGACCAAACAGTGTTGACATCGACACTGG
ATGGCGGCGTATGGGTAAAAAGCCTGAACTCACCGCGACGTCTGTCGAGA
AGTTTCTGATCGAAAAGTTCGACAGCGTCTCCGACCTGATGCAGCTCTCG
GAGGGCGAAGAATCTCGTGCTTTCAGCTTCGATGTAGGAGGGCGTGGATA
TGTCCTGCGGGTAAATAGCTGCGCCGATGGTTTCTACAAAGATCGTTATG
TTTATCGGCACTTTGCATCGGCCGCGCTCCCGATTCCGGAAGTGCTTGAC
ATTGGGGAATTCAGCGAGAGCCTGACCTATTGCATCTCCCGCCGTGCACA
GGGTGTCACGTTGCAAGACCTGCCTGAAACCGAACTGCCCGCTGTTCTGC
AGCCGGTCGCGGAGGCCATGGATGCGATGGCTGCGGCCGATCTTAGCCAG
ACGAGCGGGTTCGGCCCATTCGGACCGCAAGGGGCGTGATTTCATATGCG
CGATTGCTGATCCCCATGTGTATCACTGGCAAACTGTGATGGACGACACG
GTCAGTGCGTCCGTCGCGCAGGCTCTCGATGAGCTGATGCTTTGGGCCGA
GGACTGCCCCGAAGTCCGGCACCTCGTGCACGCGGATTTCGGCTCCAACA
ATGTCCTGACGGACAATGGCCGCATAACAGCGGTCATTGACTGGAGCGAG
GCGATGTTCGGGGATTCCCAATACGAGGTCGCCAACATCTTCTTCTGGAG
```

-continued

```
GCCGTGGTTGGCTTGTATGGAGCAGCAGACGCGCTACTTCGAGCGGAGGC

ATCCGGAGCTTGCAGGATCGCCGCGGCTCCGGGCGTATATGCTCCGCATT

GGTCTTGACCAACTCTATCAGAGCTTGGTTGACGGCAATTTCGATGATGC

AGCTTGGGCGCAGGGTCGATGCGACGCAATCGTCCGATCCGGAGCCGGGA

CTGTCGGGCGTACACAAATCGCCCGCAGAAGCGCGGCCGTCTGGACCGAT

GGCTGTGTAGAAGTACTCGCCGATAGTGGAAACCGACGCCCCAGCACTCG

TCCGAGGGCAAAGGAATAATCAGTACTGACAATAAAAAGATTCTTGTTTT

CAAGAACTTGTCATTTGTATAGTTTTTTTATATTGTAGTTGTTCTATTTT

AATCAAATGTTAGCGTGATTTATATTTTTTTAGATGCGAAGTTAAGTGC

GCAGAAAGTAATATCATGCGTCAATCGTATGTGAATGCTGGTCGCTATAC

TGCTGTCGATTCGATACTAACGCCGCCATCCAGTGTCGa
```

Assembling the insertion cassette for deletion of the Mnn 1 gene in *S. cerevisiae*:

CB39:
```
TTTATATTAAACCAAAGGTCTTTGAGATCGTGTACCATACTGCCTGCAGG

TCAACATG
```

CB42:
```
GGTGTTATCTTTATTAGCATGTGACCAAACAGTGTTGACATCGACACTGG

ATGGCGGCGT
```

11.1.1.2 Transformation of the Yeasts
Preparation of competent yeasts:
The strains were prepared as indicated above in order to make them competent.
Electroporation of *S. cerevisiae* yeasts
Procedure:
20 μg of the plasmids containing the expression cassettes for *S. cerevisiae* were digested by a restriction enzyme. The lenearized cassette was introduced into the yeasts by electroporation. The yeasts are selected on a YPD medium containing hygromycin.

11.1.2 Deletion of the Mnn9 Gene in the Yeasts Amélie, Arielle, Anaïs, Alice, Abel, Ashley, Athena, Azalée and Aurel 11.1.2.1 Construction of a Cassette for Integration Into the Mnn9 Gene Containing a Gene for Resistance to Phleomycin
Amplification of the promoter SV40 with the Mnn9 5' enc

CB46:
```
AAAGATCTTAACGTCGTCGACCATGTGGTTAAGCACGACGCAGGCAGAAG

TATGCAAA
```

CB47:
```
AAATGTCGTGATGGCAGGTTGGGCGTCGCTTGGTCGGCCATAGCTTTTTG

CAAAAGCCTAG
```

Phleomycin-terminator TEF amplification with homology to the promoter SV40

CB48:
```
GCTGTGGAATGTGIGTCAGTTAGGGTGTGGAAAGTCCCCAATGGCCGACC

AAGCGACGCCC
```

CB49:
```
GGTGTTATCTTTATTAGCATGTGAGCAAACAGTGTTGACATCGACACTGG

ATGGCGGCGT atggccgaccaagcgacgcccaacctgccatcacgagatttcgattccac ggccgccttctatgaaaggtgggcttcggaatcgttttccgggacgccg gctggatgatcctccagcgcggggatctcaagctggagttcttcgcccac cccgggctcgatccctcgcgagttggttcagctgctgcctgaggctgga cgacctcgcggagttctaccggcagtgcaaatccgtcggcatccaggaaa ccagcagcggctatccgcgcatccatgccccgaactgcaggagtgggga ggcacgatggccgctttggtcgacccggacgggacgctcctgcgcctgat acagaacgaattgcttgcaggcatctcatgatcagtactgacaataaaaa gattcttgttttcaagaacttgtcatttgtatagttttttatattgtag ttgttctattttaatcaaatgttagcgtgatttatattttttttcgcctc gacatcatctgcccagatgcgaagttaagtgcgcagaaagtaatatcatg cgtcaatcgtatgtgaatgctggtcgctatactgctgtcgattcgatact aacgccgccatccagtgtcgaaaacgagctctcgagaacccttaat
```

11.1.2.2 Transformation of the Yeasts
Preparation of competent yeasts:
The yeasts are prepared as indicated above in order to make them competent
Electroporation of *S. cerevisiae* yeasts
Procedure:
20 μg of the plasmids containing the expression cassette for *S. cerevisiae* were digested by a restriction enzyme. The linearized cassette was introduced into the yeasts by electroporation. The yeasts are selected on a YPD medium containing phleomycin.

11.2 Step 2: Dejection of the GMA12 Gene in the Yeasts *S. Pombe*, Emma, Erika, Enrique, Elga, Etienne 11.2.1 Construction of the Integration Cassette Containing the Gene for Resistance to Hygromycin ext-gma12/prom-CaMV/hph/Tef-term/ext-gma12

CB51:
```
CAAAGATCTTAACGTCGTCGACCATGTGCTTAAGCACGACTGGCTGCAGG

TGAACATG
```

CB52:
```
ATATGATCCTTTTCTTGAGCAGACATCCAATCGGATCCTTTCGACACTGG

ATGGCGGCGT
```

11.2.2 Transformation of the Yeasts
Preparation of competent yeasts:
The strains are prepared as indicated above in order to make them competent.
Electroporation of *S. cerevisiae* yeasts.
Procedure:
20 μg of the plasmids containing the expression cassette for *S. pombe* were digested by a restriction enzyme. The linearized cassette was introduced by electroporation. The yeasts are selected on an YPD medium containing hygromycin.

Example 12

Strains+Expression Cassettes for Sialylation of the N-Glycans of *S. Cerevisiae* and *S. Pombe*

With the purpose of obtaining effective sialylation of N-glycans of proteins produced in *S. cerevisiae* and *S. pombe*, first of all the biosynthesis route for sialic acid has to be introduced into the same yeasts. To do this, we introduced into the genome of the yeasts, the route for the biosynthesis of CMP-sialic acid of *N. meningitidis*, enzymes localized in the cytosol. Preparation of cassettes in tandem for sialylation (from the strains Athena, Aurel and Azalée):

12.1 Cassette S1

Construction of a tandem cassette consisting of the promoter PET56, of the ORF of sialic acid synthase, of the terminator CYC1 and then of the promoter PET565, of the ORF of CMP-sialic acid synthase and of the terminator CYC1.

Obtaining the ORFs:
Sialic acid synthase (1,050 bp)

```
Atgcaaaacaacaacgaatttaaaattggtaatcgttcagtaggttacaa
ccacgaaccattgattatctgtgaaatcggcatcaatcatgaaggctctt
taaaaacagcttttgaaatggttgatgctgcctataatgcaggcgctgaa
gttgttaaacatcaaacacacatcgttgaagacgaaatgtctgatgaggc
caaacaagtcattccaggcaatgcagatgtctctatttatgaaattatgg
aacgttgcgccctgaatgaagaagatgagattaaattaaaagaatacgta
gagagtaagggtatgattttatcagtactccttctctcgtgcagctgc
tttacgattacaacgtatggatattccagcatataaaatcggctctggcg
aatgtaataactacccattaattaaactggtggcctcttttggtaagcct
attattctctctaccggcatgaattctattgaaagcatcaaaaagtcggt
agaaattattcgagaagcaggggtaccttatgctttgcttcactgtacca
acatctacccaaccccttacgaagatgttcgattgggtggtatgaacgat
ttatctgaagcctttccagacgcaatcattggcctgtctgaccataccttt
agataactatgcttgcttaggagcagtagctttaggcggttcgattttag
agcgtcactttactgaccgcatggatcgcccaggtccggatattgtatgc
tctatgaatccggatacttttaaagagctcaagcaaggcgctcatgctt
aaaattggcacgcggcggcaaaaaagacacgattatcgcgggagaaaagc
caactaaagatttcgcctttgcatctgtcgtagcagataaagacattaaa
aaaggagaactgttgtccggagataacctatgggttaaacgcccaggcaa
tggagacttcagcgtcaacgaatatgaaacattatttggtaaggtcgctg
cttgcaatattcgcaaaggtgctcaaatcaaaaaaactgatattgaataa
```

CMP-sialic acid synthase (687 bp):

```
atggaaaaacaaaatattgcggttatacttgcgcgccaaaactccaaagg
attgccattaaaaaatctccggaaaatgaatggcatatcattacttggtc
atacaattaatgctgctatatcatcaaagtgttttgaccgcataattgtt
tcgactgatggcgggttaattgcagaagaagctaaaaatttcggtgtcga
```

```
agtcgtcctacgccctgcagagctggcctccgatacagccagctctattt
caggtgtaatacatgctttagaaacaattggcagtaattccggcacagta
accctattacaaccaaccagtccattacgcacaggggctcatattcgtga
agcttttctctatttgatgagaaaataaaaggatccgttgtctctgcat
gcccaatggagcatcatccactaaaaaccctgcttcaaatcaataatggc
gaatatgcccccatgcgccatctaagcgatttggagcagcctcgccaaca
attacctcaggcatttaggcctaatggtgcaatttacattaatgatactg
cttcactaattgcaaataattgttttttttatcgctccaaccaaactttat
attatgtctcatcaagactctatcgatattgatactgagcttgatttaca
acaggcagaaaacattcttaatcacaaggaaagctaa
```

Expression cassette:
Promoter PET56

```
CTTTGCCTTCGTTTATCTTGCCTGCTCATTTTTAGTATATTCTTCGAAG
AAATCACATTACTTTATATAATGTATAATTCATTATGTGATAATGCCAAT
CGCTAAGAAAAAAAAGAGTCATCCGCTAGGTGGAAAAAAAAAATGAAA
ATCATTACCGAGGCATAAAAAAATATAGAGTGTACTAGAGGAGGCCAAGA
GTAATAGAAAAGAAAATTGCGGGAAAGGACTGTGTT
```

12.2 Cassette S2

The expression cassette of the CMP-sialic acid transporter was produced in tandem with a cassette for resistance to an antibiotic, hygromycin. This double cassette is inserted into the mnn1 gene. Insertion of this cassette into this locus will induce resistance to hygromycin but also the deletion of the mnn1 gene.

Obtaining the ORF
CMP-sialic acid transporter from mus musculus (1,011 bp)

```
atggctccggcgagagaaaatgtcagtttattcttcaagctgtactgctt
ggcggtgatgactctggtggctgccgcttacaccgtagctttaagataca
caaggacaacagctgaagaactctacttctcaaccactgccgtgtgtatc
acagaagtgataaagttactgataagtgttggcctgttagctaaggaaac
tggcagtttgggtagatttaaagcctcattaagtgaaaatgtcttgggga
gccccaaggaactggcgaagttgagtgtgccatcactagtgtatgctgtg
cagaacaacatggccttcctggctctcagtaatctggatgcagcagtgta
ccaggtgacctatcaactgaagatcccctgcactgctttatgtactgttt
taatgttaaatcgaacactcagcaaattacagtggatttccgtcttcatg
ctgtgtggtgggcacactcgtacagtggaaaccagcccaagcttcaaa
agtcgtggtagcgcagaatccattgttaggctttggtgctatagctattg
ctgtattgtgctctggatttgcaggagtttattttgaaaaagtcttaaag
agttccgacacttcccttttgggtgagaaacattcagatgtatctgtcagg
gatcgttgtgacgttagctggtacctacttgtcagatggagctgaaattc
aagaaaaaggattcttctatggctacacgtattatgtctggtttgttatc
ttccttgctagtgtgggaggcctctacacgtcagtggtggtgaagtatac
```

```
agacaacatcatgaaaggcttctctgctgccgcagccattgttctttcta ccattgcttcagtcctactgtttggattacagataacactttcatttgca ctgggagctcttcttgtgtgtgtttccatatatctctatgggttacccag acaagatactacatccattcaacaagaagcaacttcaaaagagagaatca ttggtgtgtga
```

Construction of the expression cassette:

The expression cassette of the CMP-sialic acid transporter (promoter CaMV, ORF, terminator CYC1) is assembled with an expression cassette of resistance to hygromycin comprising the promoter of CaMV, the ORF of the resistance to hygromycin, as well as the terminator TEF. These tandem cassettes are inserted into the marker mnn1.

12.3 Cassette S3

The expression cassette for sialyl transferase ST3GAL4 was produced in tandem with a cassette for resistance to an antibiotic, phleomycin. This double cassette is inserted into the gene mnn9. Insertion of this cassette into the locus will induce resistance to hygromycin but also deletion of the mnn9 gene.

Obtaining the ORF

Human sialyl transferase ST3GAL4 (990 bp)

```
atggtcagcaagtcccgctggaagctcctggccatgttggctctggtcct ggtcgtcatggtgtggtattccatctcccgggaagacagttttattttc ccatcccagagaagaaggagccgtgcctccagggtgaggcagagagcaag gcctctaagctctttggcaactactcccgggatcagccatcttcctgcg gcttgaggattatttctgggtcaagacgccatctgcttacgagctgccct atgggaccaaggggagtgaggatctgctcctccgggtgctagccatcacc agctcctccatccccaagaacatccagagcctcaggtgccgccgctgtgt ggtcgtggggaacgggcaccggctgcggaacagctcactgggagatgcca tcaacaagtacgatgtggtcatcagattgaacaatgcccagtggctggc tatgagggtgacgtgggctccaagaccaccatgcgtctcttctaccctga atctgcccacttcgaccccaaagtagaaaacaacccagacacactcctcg tcctggtagctttcaaggcaatggacttccactggattgagaccatcctg agtgataagaagcgggtgcgaaagggtttctggaaacagcctcccctcat ctgggatgtcaatcctaaacagattcggattctcaacccttcttcatgg agattgcagctgacaaactgctgagcctgccaatgcaacagccacggaag attaagcagaagcccaccacgggcctgttggccatcacgctggccctcca cctctgtgacttggtgcacattgccggctttggctacccagacgcctaca acaagaagcagaccattcactactatgagcagatcacgctcaagtccatg gcggggtcaggccataatgtctcccaagaggccctggccattaagcggat gctggagatgggagctatcaagaacctcacgtccttctga
```

Murine sialyl transferase ST3GAL4 (1,002 bp)

```
atgaccagcaaatctcactggaagctcctggccctggctctggtccttgt tgttgtcatggtgtggtattccatctcccgagaagataggtacattgagt tcttttatttcccatctcagagaagaaagagccatgcttccagggtgag
```

```
gcagagagacaggcctctaagattttggcaaccgttctagggaacagcc catctttctgcagcttaaggattattttgggtaaagacgccatccacct atgagctgccctttgggactaaaggaagtgaagaccttcttctccgggtg ctggccatcactagctattctatacctgagagcataaagagcctcgagtg tcgtcgctgtgttgtggtgggaaatgggcaccggttgcggaacagctcgc tgggcggtgtcatcaacaagtacgacgtggtcatcagattgaacaatgct cctgtggctggctacgagggagatgtgggctccaagaccaccatacgtct cttctatcctgagtcggcccactttgaccctaaaatagaaaacaacccag acacgctcttggtcctggtagctttcaaggcgatggacttccactggatt gagaccatcttgagtgataagaagcgggtgcgaaaaggcttctggaaaca gcctcccctcatctgggatgtcaaccccaaacaggtccggattctaaacc ccttctttatggagattgcagcagacaagctcctgagcctgcccatacaa cagcctcgaaagatcaagcagaagccaaccacgggtctgctagccatcac cttggctctacacctctgcgacttagtgcacattgctggctttggctatc cagatgcctccaacaagaagcagaccatccactactatgaacagatcaca cttaagtctatggcgggatcaggccataatgtctcccaagaggctatcgc catcaagcggatgctagagatgggagctgtcaagaacctcacatacttct ga
```

The expression cassette of the CMP-sialic acid transporter (promoter CaMV, ORF, terminator CYC1) is assembled with an expression cassette of resistance to hygromycin comprising the promoter of CaMV, the ORF of the resistance to hygromycin as well as the terminator TEF. These tandem cassettes are inserted into the marker mnn1.

Example 13

Production of Homogeneously Glycosylated EPO 13.1 Amplification of the Nucleotide Sequence of Human Erythropoietin (EPO)

Amplification of the nucleotide sequence of human EPO was obtained from complementary DNA of human kidney with suitable primers.

13.2 Cloning of the Sequence of the EPO in an Expression Vector of *S. Cerevisiae*

The nucleotide sequence of human huEPO truncated of its STOP codon (585 base pairs) is integrated into an expression vector of the yeast *S. cerevisiae*. The continuity of the reading frame between the introduced sequence and the sequence of the plasmid pSC (epitope V5 and poly-histidine tag) was confirmed by sequencing the obtained plasmid (pSC-EPO). The expression of the protein EPO is found under the control of the promoter pGAL1, a promoter inducible by galactose for *S. cerevisiae* strains. The selection of the yeasts having the plasmid is performed by return of prototrophy for uracil (presence of the URA3 sequence in the plasmid).

Sequence obtained in the expression plasmid:

(SEQ ID No 11)
```
  1 ATGGGGGTGC ACGAATGTCC TGCCTGGCTG TGGCTTCTCC TGTCCCTGCT

51 GTCGCTCCCT CTGGGCCTCC CAGTCCTGGG CGCCCCACCA CGCCTCATCT

101 GTGACAGCCG AGTCCTGGAG AGGTACCTCT TGGAGGCCAA GGAGGCCGAG

151 AATATCACGA CGGGCTGTGC TGAACACTGC AGCTTGAATG AGAATATCAC

201 TGTCCCAGAC ACCAAAGTTA ATTTCTATGC CTGGAAGAGG ATGGAGGTCG

251 GGCAGCAGGC CGTAGAAGTC TGGCAGGGCC TGGCCCTGCT GTCGGAAGCT

301 GTCCTGCGGG GCCAGGCCCT GTTGGTCAAC TCTTCCCAGC CGTGGGAGCC

351 CCTGCAGCTG CATGTGGATA AAGCCGTCAG TGGCCTTCGC AGCCTCACCA

401 CTCTGCTTCG GGCTCTGGGA GCCCAGAAGG AAGCCATCTC CCCTCCAGAT

451 GCAGCCTCAG CTGCTCCGCT CCGAACAATC ACTGCTGACA CTTTCCGCAA

501 ACTCTTCCGA GTCTACTCCA ATTTCCTCCG GGGAAAGCTG AAGCTGTACA

551 CAGGGGAGGC CTGCAGGACA GGCGACAGAA AGGGCGAGCT TCGAGGTCAC

601 CCATTCGAAG GTAAGCCTAT CCCTAACCCT CTCCTCGGTC TCGATTCTAC

651 GCGTACCGGT CATCATCACC ATCACCATTG A
```

Protein sequence of the sequenced EPO in the expression plasmid (SEQ ID No 12)

MGVHEGPAWLWLLLSLLSLPLGLPVLGAPPRLICDSRVLERYLLEAKEAE

NITTGCAEHCSLNENITVPDTKVNFYAWKRMEVGQQAVEVWQGLALLSEA

VLRGQALLVNSSQPWEPQLHVDKAVSGLRSLTTLLRALGAQKEAISPPDA

ASAAPLRTITADTFRKLFRVYSNFLRGKLKLYTGEACRTGDRKGELRGHP

FEGKPIPNPLLGLDSTRTGHHHHHH*
                     Epitope V5    poly-HIS

13.3 Extraction of the RNAs

Centrifuge the yeasts 16000 g for 5 min. Remove the supernatant and re-suspend the pellets in 500 µL of TES buffer (10 mM TrisHCl pH7.5 10 mM EDTA, 0.5% SDS). Add 200 µL of phenol and 200 µL of chloroform and then incubate for 20 min at 65° C. by vortexing for 30 s every 5 min and incubate for 1 hr at −80° C. Centrifuge for 20 min at 13,200 rpm and then recover the aqueous phase and add 335 µL of phenol and 67 µL of chloroform. Vortex and centrifuge for 5 min at 11,000 rpm. Recover the aqueous phase and add 300 µL of chloroform. Vortex and centrifuge for 2 min at 13,200 rpm. Recover the aqueous phase and add 30 µL of 3M sodium acetate at pH 5.2 and 600 µL of absolute ethanol. Incubate for 1 hr at −20° C. Centrifuge for 15 min at 13,200 rpm. Remove the supernatant while being careful with the pellet. Leave them to dry, take them up in 100 µL of EDPC water and then place them in a tube containing the violet Nucleospin (Nucleospin RVAII) filtration unit. Centrifuge for 1 min at 11,000 g. Remove the filter and add 350 µL of 70% ethanol. Load the Nucleospin RNAII column. Centrifuge for 30 s at 8000 g. Place the column in a new tube, add 350 µL of Membrane Desalting Buffer. Centrifuge for 1 min at 11,000 g. Deposit 95 µL of DNase solution at the centre of the column, and then incubate for 15 min at room temperature. Add 200 µL of RA2 solution (inactivate the DNase) and centrifuge for 30 s at 8,000 g. Add 600 µL of RA3 solution to the centre of the column. Centrifuge for 30 s at 8,000 g. Place the column in a new tube, add 250 µL of RA3 solution. Centrifuge for 2 min at 11,000 g in order to drive the column. Place the column in a 1.5 nL tube and add 50 µL of DEPC water. Centrifuge for 1 min at 11,000 g. Store the samples at −80° C.

13.4 Reverse transcription: Super Script III First-Strand Synthesis System for RT-PCR

| | | |
|---|---|---|
| 5 µg of RNA | | At most 8 µL |
| Random hexamer | 50 ng/µL | 1 µL |
| dNTP mix | 10 mM | 1 µL |
| DEPC water | | qsp 10 µL |
| Incubate for 5 min at 65° C. | | |
| Add 10 µL of transcription mix: | | |
| RT Buffer | 10X | 2 µL |
| MgCl₂ | 25 mM | 4 µL |
| DTT | 0.1M | 2 µL |
| RNase Out | 40 U/µL | 1 µL |
| SuperScript | 200 U/µL | 1 µL |
| Incubate | | |
| For 10 min at 25° C. | | |
| For 50 min at 50° C. | | |
| For 5 min at 85° C. | | |

Recover in ice and add 1 µL of RNaseH. Leave to incubate for 20 min at 37° C. and then store the cDNAs at −20° C.

13.5 Extraction of the Proteins

After centrifugation at 1,500 g for 5 min at 4° C., the cell pellet is taken up in 500 µL of sterile H₂O and then centrifuged at maximum speed for 30 s at 4° C. The pellet is taken up into 500 µL of sodium phosphate 50 mM lysis buffer, pH 7.4, 5% glycerol, 1 mM PMSF, centrifuge for 10 min at 1,500 g at 4° C. The pellet is then taken up in a volume of lysis buffer required for obtaining an OD comprised between 50 and 100. The samples are then vortexed for 4×30 s with glass beads and centrifugation for 10 min at maximum speed is carried out in order to separate the beads and the cell debris from the protein supernatant. A BCA assay is carried out on the supernatant.

13.6 Purification of EPO

The total proteins are first of all dialyzed against the 10 mM Tris HCl buffer, pH 6.0. After equilibration of a cation exchanger SP Sephadex C50 column with 10 mM Tris-HCl pH 6.0, the total dialyzed proteins are loaded on the column. After rinsing the column with 10 mM Tris HCl buffer pH 6.0, the proteins are eluted with 10 mM Tris HCl buffer pH 6.0, 250 mM NaCl. The absorbance of each fraction is determined at 280 nm as well as the amount of proteins eluted by a Bradford assay. The proteins are then analyzed by SDS-PAGE electrophoresis on 12% acrylamide gel.

13.7 Detection of the EPO Protein—Western Blot

The total proteins are transferred onto a nitrocellulose membrane in order to proceed with detection by the anti-EPO antibody (R&D Systems). After the transfer, the membrane is saturated with a blocking solution (TBS, 1% blocking solution (Roche)) for 1 hour. The membrane is then put into contact with the anti-EPO antibody solution (dilution 1:500) for 1 hour. After three rinses with 0.1% Tween 20-TBS the membrane is put into contact with the secondary anti-mouse-HRP antibody in order to proceed with detection by chemiluminescence (Roche detection solution).

141. Results 14.1: Validation of the Clones Having Integrated the Kanamycin Cassette in the Och1 Gene For suppressing the Och1 activity, the introduced cassette was entirely sequenced after its integration in order to map the affected genomic region in the genome of the yeast. Absence of enzymatic activity is then achieved, enhancing the previous results, and then the structure of the glycans is determined by mass spectrometry.

Figure 3:
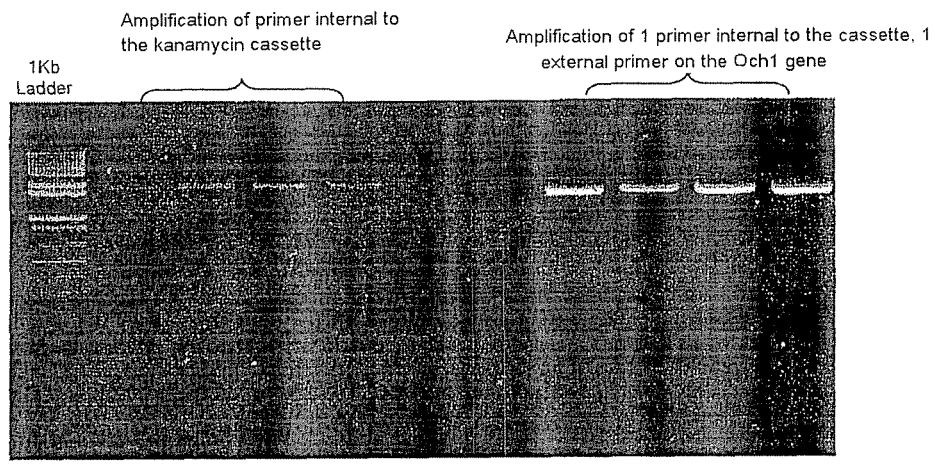
FIG. 3: PCR analysis of och1:Kan$^R$ transformants.

The analysis on 1% agarose-TBE gel of the PCR reaction carried out from genomic DNA of S. cerevisiae clones having resisted to the presence of kanamycin in the culture medium shows an amplified 2 kb fragment with a specific pair of oligonucleotides of the kanamycin cassette. The size of this fragment corresponds to the theoretical size of the kanamycin cassette. The second fragment was amplified by means of an oligonucleotide internal to the kanamycin cassette and an oligonucleotide external to the cassette hybridizing with the Och1 gene. The theoretical size of the expected fragment is 1.5 kb which corresponds to the size of the obtained fragment. We may therefore conclude that the clones 1, 2, 3 and 4 have actually integrated the kanamycin cassette and that the latter was integrated into the Och1 gene (see FIG. 3).

The same type of PCR reaction was carried out on the S. pombe strains having resisted to the presence of kanamycin in the culture medium. Thus, two mutated clones of each strain were isolated and tested for loss of α1,6-mannosyl transferase enzymatic activity.

Test of Mannosyl Transferase Och1 Activity on Strains of Mutated Yeasts

Figure 4:
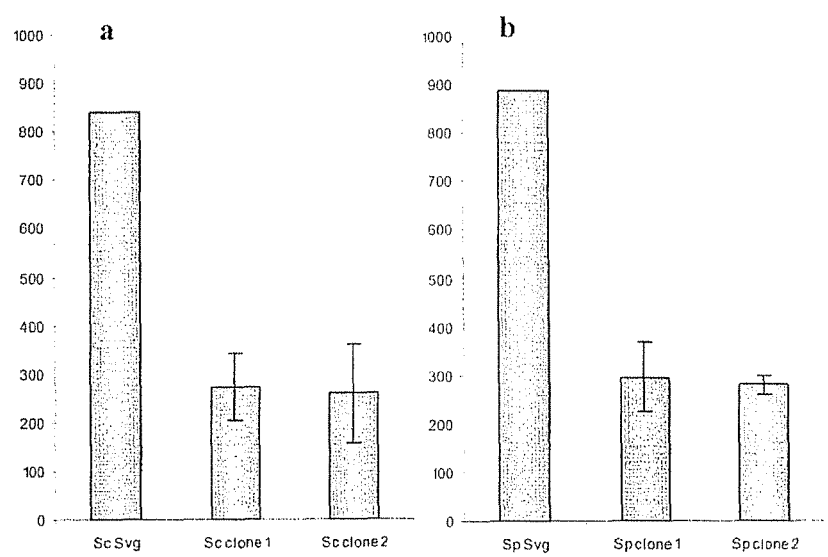
FIG. 4: Och1-activity assay in wild-type and PCR-selected transformants; a) S. cerevisiae, b) S. pombe.

Validation of the loss of Och1 activity in the mutant Δoch1 obtained by homologous recombination in the S. cerevisiae and S. pombe yeasts:

After validation by PCR of the insertion of the expression cassette of kanamycin in wild S. cerevisiae and wild S. pombe yeasts, the positive clones to this insertion are tested for their loss of mannosyl transferase Och1 activity. The Och1 activity was tested on microsomes of the S. cerevisiae and S. pombe yeasts. FIG. 4 shows the Och1 activity test on a—the microsomal fraction of the wild strain and of the selected clones of S. cerevisiae, b—the microsomal fraction of the wild strain and of selected clones of S. pombe. According to FIG. 4, we may observe a loss of activity of the Och1 enzyme in the selected clones of S. cerevisiae (a) and S. pombe (b).

Validation of the Strains by Analyses of N-Glycans

Figure 5:
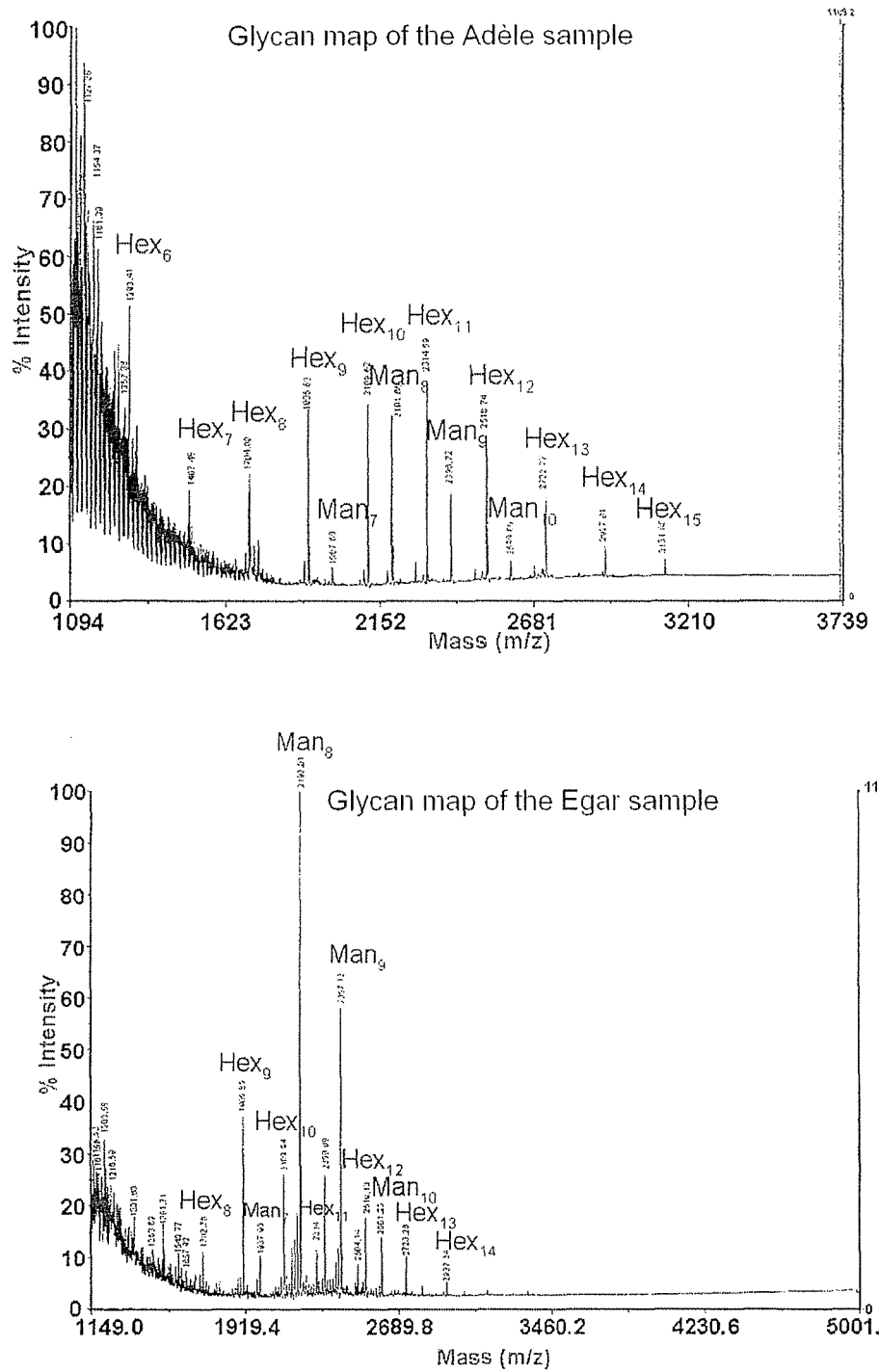
FIG. 5: MALDI-TOFF mass spectrometry N-glycan analysis of total proteins in Adele and Edgar strains.

The total proteins from both modified strains were reduced and alkylated and then digested by trypsin. The free polysaccharides are removed by passing over SepPak C18. The recovered peptides and glycopeptides are subject to PNGase. The glycans are purified on SepPak C18 and then methylated before being analyzed by mass spectrometry in the Maldi-Tof mode. FIG. 5 shows the mass spectrum carried on N-glycans from the strains Adele and Edgar.

Nomenclature of the Yeasts:

S. cerevisiae Δoch1=Adèle

S. pombe Δoch1=Edgar

Both strains have N-glycans with oligomannoside forms from $Man_7$ to $Man_{10}$, shorter forms than in the wild strain of Saccharomyces cerevisiae indicating the loss of wild polymannosylated forms.

The predominant structures for the Edgar strain (Δoch1) are $Man_9$ and $Man_8$, structures which are conventionally encountered in mammals after transit of the neosynthesized protein into the endoplasmic reticulum. This suggests blocking of glycosylation due to the impossibility of action of the Golgian mannosyl transferases which only graft mannose on glycans on which the enzyme Och1 has grafted a mannose attached in the α1,6 position.

Figure 6:
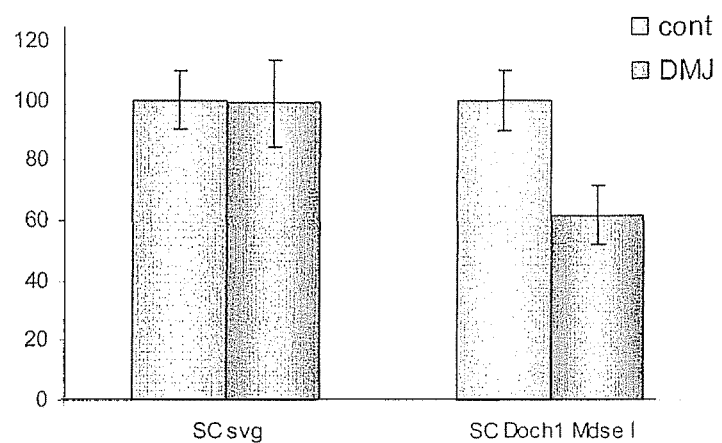
FIG. 6: Mannosidase I-activity assay in wild-type and PCR-selected transformants in presence and absence of DMJ, an inhibitor of alpha-1,2-mannosidase I activity; SC=S. cerevisiae, SP=S. pombe.
Figure 6:
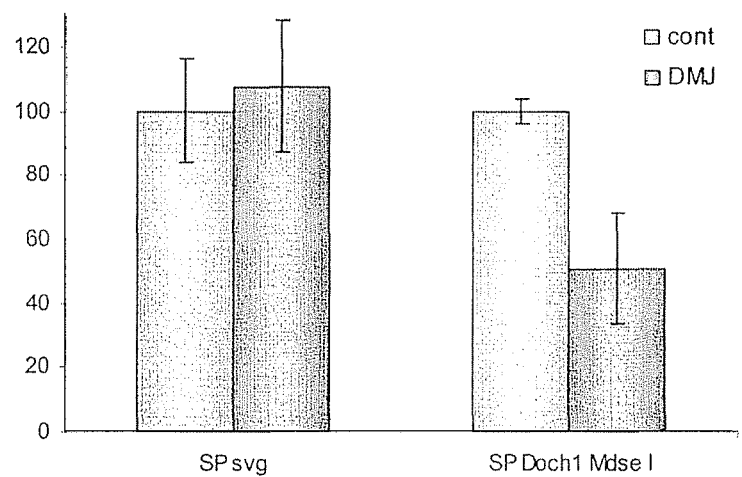

14.2: Validation of the Clones Having Integrated the Mannosidase I Cassette into the URA3 Gene The Adèle and Edgar yeasts, positive for the insertion of the expression cassette of mannosidase I in the gene URA3, are tested for their mannosidase I biochemical activity. FIG. 6 shows the assay of mannosidase activity in microsomes of S. cerevisiae and S. pombe yeasts. The experiment was conducted in triplicate. We may observe in the wild S. cerevisiae and S. pombe strains, a mannosidase activity non-inhibited by DMJ. Conversely, the selected strains have significant inhibition of mannosidase activity measured during a DMJ treatment. Further, as the measured mannosidase I activity is present in the microsomes of yeasts, we may infer that this enzyme is expressed in the secretion route at the cis-Golgi/endoplasmic reticulum, indicating that the HDEL retention signal integrated in the C-terminus of the protein is well recognized by the cell system.

Nomenclature of the Yeasts:

S. cerevisiae Adèle+mannosidase I=Amélie

Figure 7:
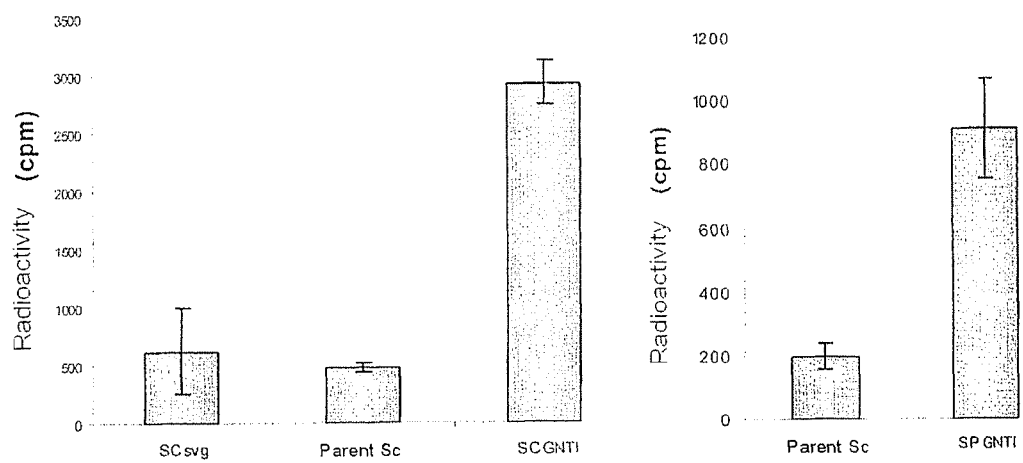
FIG. 7: GlcNAc Transferase I-activity assay in wild-type and PCR-selected transformants; SC=S. cerevisiae, SP=S. pombe.

S. pombe Edgar+mannosidase I=Emma 14.3 Validation of the Clones Having Integrated the N-Acetylglucosaminyl Transferase (GlcNAc Transferase I) Cassette in the Modified Yeasts FIG. 7 shows the GlcNAcTransferase I activity in microsomes of wild and modified yeasts.

In the microsomes or fractions of the Amélie-GlcNacTI and Emma-GlcNacTI yeasts, we observe an increase in the labeling of the acceptor by transfer of a radioactive GlcNAc group compared with the labeling observed in control yeasts (wild and/or Δoch1-MdseI yeasts). This transfer involves the presence of N-acetylglucosaminyl transferase activity in the yeasts modified by expression of GlcNAcTI.

Nomenclature of the Modified Yeasts:

S. cerevisiae Amélie+GlcNAcTI=Agathe

Figure 8:
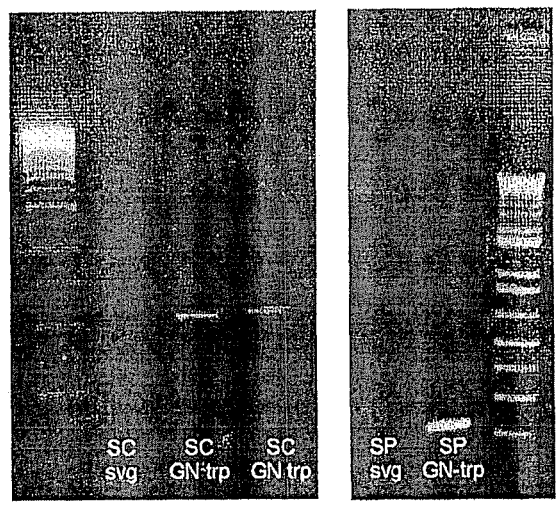
FIG. 8: RT-PCR analysis of S. cerevisiae (SC) and S. pombe (SP) clones transformed with the UDP-GlcNAc transporter expression cassette.

S. pombe Emma+GlcNAcTI=Egée 14.4 Validation of the Clones Having Integrated the Cassette of the UDP-GlcNAc Transporter in the Modified Yeasts The expression of the UDP-GlcNAc transporter was analyzed by RT-PCR on parent or modified yeast cultures. After a reverse transcription step on the total extracted RNAs, the cDNAs were analyzed by PCR by using specific primers of the UDP-GlcNAc transporter (nested PCR). Therefore, an expression of the mRNA of this transporter is observed in the yeasts modified by the expression cassette of the UDP-GlcNAc transporter (FIG. 8).

Nomenclature of the Modified Yeasts:

*S. cerevisiae* Agathe+UDP-GlcNAc transporter=Arielle

*S. pombe* Egée+UDP-GlcNAc transporter=Erika

14.5 Validation of Clones Having Integrated the Cassette of Mannosidase II in the Modified Yeasts a—Validation by PCR Amplification The selected clones for *S. cerevisiae* and *S. pombe* were tested by PCR in order to check the presence of expression cassettes of mannosidase II in the genome of the yeasts.

b—Expression of Mannosidase II

The expression of mannosidase II was analyzed by RT-PCR on parent or modified yeast cultures. After a step of reverse transcription on the extracted RNAs, the cDNAs were analyzed by PCR by using specific mannosidase II primers (nested PCR). In the yeasts modified by the expression cassette of mannosidase II an expression of the mRNA of this protein is therefore observed.

c—Measurement of the Activity of Mannosidase II

The Adèle and Edgar yeasts, positive for insertion of the expression cassette of mannosidase II, are tested for their mannosidase II biochemical activity.

Figure 9:
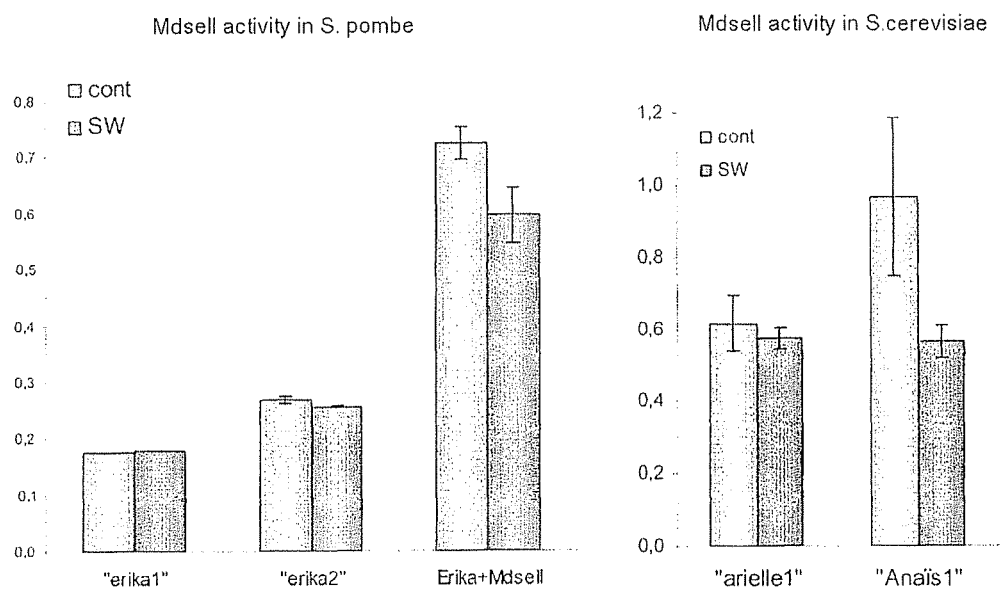
FIG. 9: Mannosidase II-activity assay in wild-type and PCR-selected transformants in presence and absence of swainsonine, an inhibitor of mannosidase II activity; SC=S. cerevisiae, SP=S. pombe.

According to FIG. 9, we may observe in the parent *S. cerevisiae* and *S. pombe* strains a mannosidase activity insensitive to the inhibitory action of swainsonine. Conversely, the selected strains have significant inhibition of mannosidase activity measured upon treatment with swainsonine. Further as, the measured mannosidase II activity is detected in Golgian yeast fractions, we may infer that this enzyme is properly expressed in the secretion route at the Golgian system.

Nomenclature of the Modified Yeasts:

*S. cerevisiae* Arielle+Mannosidase *II*=Anaïs

*S. pombe* Erika+Mannosidase *II*=Enrique

14.6 Validation of the Clones Having Integrated the N-Acetylglucosaminyl Transferase II Cassette (GlcNAc Transferase II) in Modified Yeasts a—Validation by PCR Amplification The clones selected for *S. cerevisiae* and *S. pombe* were tested by PCR in order to check for the presence of expression cassettes of the GlcNAc transferase II in the genome of the yeasts (results not shown).

b—Expression of GlcNAc Transferase II

The expression of GlcNAc transferase II was analyzed by RT-PCR on parent or modified yeast cultures. After a step of reverse transcription on the extracted RNAs, the cDNAs were analyzed by PCR by using specific primers of GlcNAc transferase II (nested PCR). An expression of the transcribed mRNA is therefore observed in the yeasts modified by the expression cassette of GlcNAc transferase II (results not shown).

Nomenclature of the Modified Yeasts:

*S. cerevisiae* Anaïs+GlcNAc transferase *II*=Alice

*S. pombe* Enrique+GlcNAc transferase *II*=Elga

14.7 Validation of the Clones Having Integrated the Galactosyl Transferase I Cassette a—Validation by PCR Amplification The clones selected for *S. cerevisiae* and *S. pombe* were tested by PCR in order to check for the presence of expression cassettes of the GalTI in the genome of the yeasts (results not shown).

b—Expression of Galactosyl Transferase I

The expression of GalTI was analyzed by RT-PCR on parent or modified yeast cultures. After a step of reverse transcription on the extracted RNAs, the cDNAs were analyzed by PCR by using specific primers of GalTI (nested PCR). An expression of the transcribed mRNA is therefore observed in the yeasts modified by the expression cassette of GalTI (results not shown).

c—Activity of the GalTI

After extraction of the total proteins of the modified yeasts, 2 µg of proteins are deposited on a nitrocellulose membrane. The membrane is then incubated with *erythrina cristagalli* lectin coupled with biotin, a lectin specifically recognizing the galactose of the Gal-$\beta$-1,4-GlcNAc unit present on glycans of glycoproteins. The membrane is put into contact with streptavidin coupled to horse radish peroxidase (HRP) in order to proceed with detection by chemiluminescence (Roche detection solution).

14.8 Validation of the Clones Having Integrated the Cassette of the GDP-Fucose Transporter a—Validation by PCR Amplification The clones selected for *S. cerevisiae* and *S. pombe* were tested by PCR in order to check for the presence of expression cassettes of the GDP-fucose transporter in the genome of the yeasts.

b—Expression of GDP-Fucose Transporter

Figure 10:
FIG. 10: RT-PCR analysis of S. cerevisiae (SC) and S. pombe (SP) clones transformed with the GDP-fucose transporter expression cassette.

The expression of GDP-fucose transporter was analyzed by RT-PCR on parent modified yeast cultures. After a step of reverse transcription on the extracted RNAs, the cDNAs were analyzed by PCR by using specific primers of the GDP-fucose transporter (nested PCR). An expression of the transcribed mRNA is therefore observed in the yeasts modified by the expression cassette of GDP-fucose transporter (FIG. 10).

Nomenclature of the Modified Yeasts:

*S. cerevisiae* Anaïs+GDP-fucose transporter=Apolline

*S. pombe* Enrique+GDP-fucose transporter=Epiphanie

14.9 Validation of the Clones Having Integrated the Cassette of Fucosyl Transferase 8 (FUT8)

a—Validation by PCR Amplification

The clones selected for *S. cerevisiae* and *S. pombe* were tested by PCR in order to check for the presence of expression cassettes of FUT8 in the genome of the yeasts.

b—Expression of the FUT8

The expression of the FUT8 was analyzed by RT-PCR on parent or modified yeast cultures. After a step of reverse transcription on the extracted RNAs, the cDNAs were analyzed by PCR by using specific primers of FUT8 (nested PCR). An expression of the transcribed mRNA is therefore observed in the yeasts modified by the expression cassette of FUT8 (results not shown).

Nomenclature of the Modified Yeasts:

*S. cerevisiae* Apolline+FUT8=Ashley

*S. pombe* Epiphanie+FUT8=Esther

14.10 Particular Case of EPO Expression in the Amélie Strain

Figure 11:
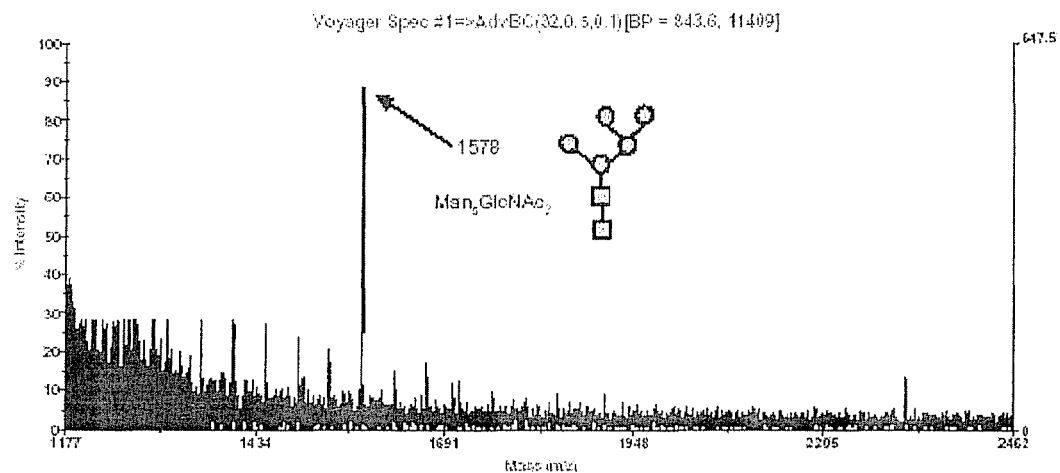
FIG. 11: MALDI-TOFF mass spectrometry N-glycan analysis of rhuEPO expressed in the Amèlie strain.

The Amélie strain has the capability of exclusively producing the N-glycan $Man_5GlcNAc_2$ (FIG. 11), a structure encountered in mammals, described as a glycan of a simple type; and being used as a basis for elaborating more complex glycans bearing galactose, fucose or sialic acid. The presence of each genomic modification in this strain is described above. Each of these steps enters a "package" of verifications consisting of selecting the best producing clone and of maximizing the percentage of chances in order to obtain an exploitable clone. The method used allows a complete control of the genetic modification procedure: the sequence to be integrated is perfectly known, just like the target genomic region of the future integration. The latter site is moreover subject to extensive research as to the effects of possible breakage, this is why the whole of the targets is finally selected for the absence of phenotype effects obtained after their breakage.

An entire procedure for tracking the genomic stability of the producing clones is performed: after each production: regular planting out of the clones on the drastic media initially used for their selection, and starting out again the validation procedure. All the expression cassettes are cloned so that in the case of genomic rearrangement of a given strain, it may be proceeded with genetic upgrade of the organism. The procedures for integrating cassettes are not standardized and it is possible to imagine production of the strains "on demand" in order to achieve specific glycosylation, as ordered by the user.

The Amélie strain is the clone which should be used as a basis for elaborating any other strain intended for producing humanized hybrid or complex glycans.

The plasmid used for the expression of EPO in the modified yeasts contains the promoter Gal1. This promoter is one of the strongest promoters known in *S. cerevisiae* and is currently used for producing recombinant proteins. This promoter is induced by galactose and repressed by glucose. Indeed, in a culture of *S. cerevisiae* yeasts in glycerol, addition of galactose allows induction of the GAL genes by about 1,000 times. If glucose is added to this culture in the presence of galactose, the GAL genes will no longer be induced, only to 1% of the level obtained with galactose alone (Johnston, M. (1987) Microbiol. Rev.). The integrated sequence of human EPO in our plasmid was modified in 5' by adding an epitope V5 as well as a polyhistidine tag in order to facilitate detection and purification of the produced protein.

The yeasts used for producing human EPO are first of all cultivated in a uracil drop out YNB medium, 2% glucose until an OD>12 is reached. After 24-48 hours of culture, 2% galactose is added to the culture in order to induce the production of our protein of interest. Samples are taken after 0, 6, 24 and 48 hours of induction.

Expression of the mRNA of EPO in Modified Yeasts

Figure 12:
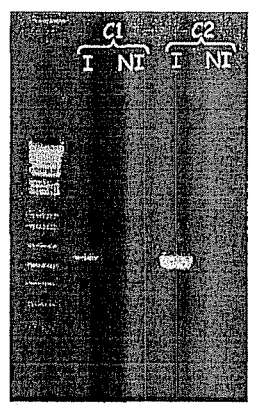
FIG. 12: RT-PCR analysis of rhuEPO expression in pGAL-rhuEPO transformants grown with (lanes 1 and 3) galactose or with glucose (lanes 2 and 4).

RT-PCR analysis of the total extracted RNAs shows expression of the messenger RNA or EPO in the clones of yeasts transformed after induction by galactose (FIG. 12 bands 1 and 3) unlike what is observed in yeasts modified without induction by galactose (FIG. 12 bands 2 and 4). The presence of galactose therefore causes induction of the transcription of the EPO gene. The sequencing of this amplified fragment confirms the production of a proper mRNA.

Purification of the EPO Protein Expressed in the Modified Yeasts

Figure 13:
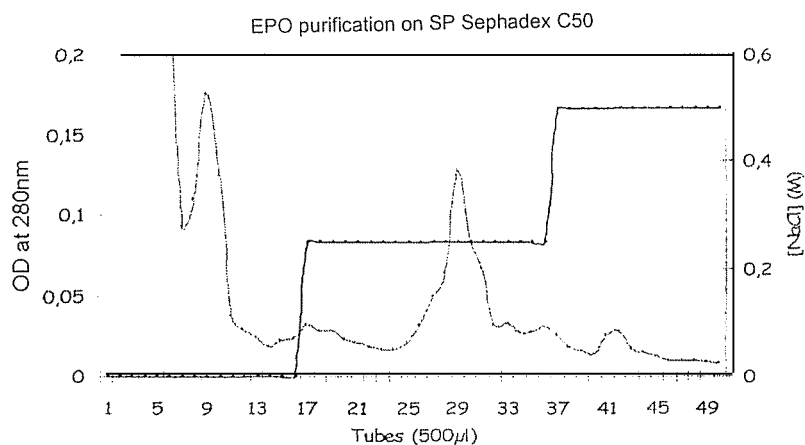
FIG. 13: Purification of rhuEPO by ion exchange chromatography (Sephadex C-50).

The total proteins obtained after induction of the expression of the rhuEPO protein by galactose are then deposited on a Sephadex C50 resin equilibrated to pH 6. Absorbance at 280 nm is determined at the column outlet (FIG. 13). The proteins eluted from the column are analyzed by SDS-PAGE electrophoresis on 12% acrylamide gel.

Figure 14:
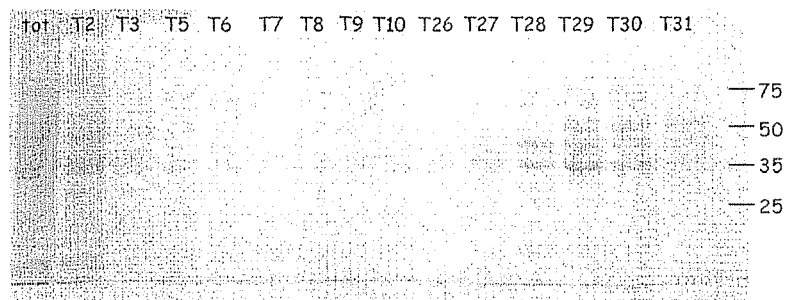
FIG. 14: SDS-PAGE analysis of the ion exchange chromatography fractions.

After migration of the SDS-PAGE gel, analysis of the proteins is accomplished either by staining with Coomassie blue (FIG. 14) or by western blot. In this case, the proteins are transferred on a nitrocellulose membrane in order to proceed with detection by the anti-EPO antibody (R&D Systems).

Figure 15:
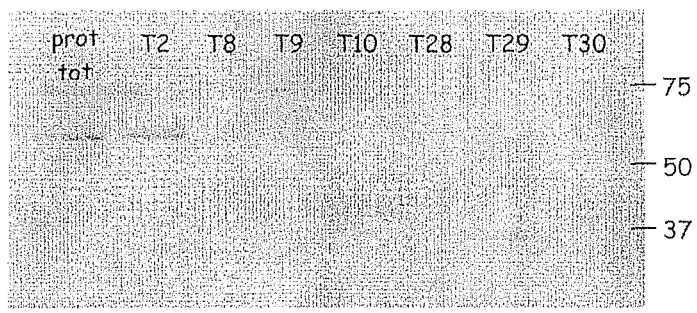
FIG. 15: Western blot analysis of the ion exchange chromatography fractions with an anti-EPO antibody.

FIG. 15 shows the presence of a protein at about 35 kDa. This protein is the majority protein in Coomassie staining and is revealed by an anti-EPO antibody in a western blot analysis (tube 29 at the column outlet).

All these results therefore show production of EPO protein by genetically modified yeasts.

---

SEQUENCE LISTING

```
<160> NUMBER OF SEQ ID NOS: 27

<210> SEQ ID NO 1
<211> LENGTH: 1644
<212> TYPE: DNA
<213> ORGANISM: Caenorhabditis elegans
<220> FEATURE:
<221> NAME/KEY: misc_feature
<223> OTHER INFORMATION: alpha-1-2 mannosidase I

<400> SEQUENCE: 1
aaagcaggca tgggcctccg atcacacgaa caacttgtcg tgtgtgtcgg agttatgttt      60
cttctgactg tctgcatcac agcgtttttc tttcttccgt caggcggcgc tgatctgtat     120
ttccgagaag aaaactccgt tcacgttaga gatgtgctta tcagagagga aattcgtcgt     180
aaagagcaag atgagttacg gcggaaagcc gaagaagcca atcccattcc aattccaaaa     240
cctgaaattg gagcatcaga tgatgcagaa ggacgaagaa ttttcgtgaa acaaatgatt     300
aaattcgcat gggacggata tcggaaatat gcctggggg agaatgaatt gaggcccaac     360
agtagatcag gacattcttc atcgatattt gggtatggaa agacgggtgc aacaattatt     420
```

-continued

```
gatgctattg atacattgta tttggttgga ttaaagaag aatataaaga ggccagagac      480
tggattgctg attttgattt caaaacgtct gcgaaaggag atctatcagt ttttgaaaca      540
aatatccgat tcactggtgg cctactctcc gcatttgcac ttaccggaga caaaatgttc      600
ttgaagaaag cagaagatgt ggcaactatt cttcttccgg cttttgaaac tccttctgga      660
ataccaaatt cattaattga tgctcaaaca ggaagatcca aaacgtatag ttgggcaagc      720
ggaaaggcaa ttctctcgga atacggttca attcaacttg aattcgatta tctctccaat      780
ctgactggaa atccagtttt tgctcaaaaa gctgataaaa taagagatgt tttaactgca      840
atggagaaac cagaaggact ttatccaatt tatattacta tggataatcc accaagatgg      900
ggacaacatc tttctcaat gggtgcaatg gctgacagtt ggtatgaata tctgctcaaa       960
caatggattg ccactggtaa aaagatgat cgcacgaaaa gagaatacga agaagcgata      1020
tttgcaatgg aaaacgaat gcttttcaaa tcggaacagt cgaatctttg gtatttcgca      1080
aaaatgaacg aaatcgcat ggaacattca tttgaacatc ttgcatgctt ttccggtgga      1140
atggttgttc ttcatgcaat gaatgagaaa aataaaacaa tatcagatca ttatatgacg      1200
ttgggaaaag aaattggtca tacatgtcat gaatcgtacg ctagatccac aactggaatc      1260
ggcccagaat ccttccaatt cacatcgagt gtagaggcaa aaacagaacg tcgtcaggat      1320
tcatattata ttcttcgtcc tgaagtcgtt gagacatggt tctacttgtg gagggctaca      1380
aaagacgaga aatatcgaca atgggcttgg gatcatgttc aaaatttgga ggagtattgt      1440
aagggcactg ccggatactc tggaatccga aacgtctacg aatcgagccc ggaacaagat      1500
gatgtgcagc agtcattcct cttcgctgag ctcttcaaat atctgtattt aattttcagt      1560
gaagataaca ttcttccact tgatcaatgg gttttcaata ccgaagctca tccattccgc      1620
attcggcatc acgacgagtt gatt                                             1644
```

<210> SEQ ID NO 2
<211> LENGTH: 1387
<212> TYPE: DNA
<213> ORGANISM: Homo sapiens
<220> FEATURE:
<221> NAME/KEY: misc_feature
<223> OTHER INFORMATION: N-acetyl-glucosaminyl transferase I comprising the cytoplasmic domain of Mnn9 for a localization in the Golgi apparatus

<400> SEQUENCE: 2

```
atgtcacttt ctcttgtatc gtaccgccta agaaagaacc cgtgggttaa cgcagggctt       60
gtgctgtggg gcgctatcct ctttgtggcc tggaatgccc tgctgctcct cttcttctgg      120
acgcgcccag cacctggcag gccacccctca gtcagcgctc tcgatggcga ccccgccagc      180
ctcacccggg aagtgattcg cctggcccaa gacgccgagg tggagctgga gcggcagcgt      240
gggctgctgc agcagatcgg ggatgccctg tcgagccagc gggggagggt gcccaccgcg      300
gcccctcccg cccagccgcg tgtgcctgtg accccgcgc cggcggtgat tcccatcctg      360
gtcatcgcct gtgaccgcag cactgttcgg cgctgcctgg acaagctgct gcattatcgg      420
ccctcggctg agctcttccc catcatcgtt agccaggact gcgggcacga ggagacggcc      480
caggccatcg cctcctacgg cagcgcggtc acgcacatcc ggcagcccga cctgagcagc      540
attgcggtgc cgcggaccca ccgcaagttc cagggctact acaagatcgc gcgccactac      600
cgctgggcgc tggccaggt cttccggcag tttcgcttcc ccgcggccgt ggtggtggag      660
gatgacctgg aggtggcccc ggacttcttc gagtactttc gggccaccta tccgctgctg      720
aaggccgacc cctccctgtg gtgcgtctcg gcctggaatg acaacggcaa ggagcagatg      780
```

```
gtggacgcca gcaggcctga gctgctctac cgcaccgact ttttccctgg cctgggctgg      840
ctgctgttgg ccgagctctg ggctgagctg gagcccaagt ggccaaaggc cttctgggac      900
gactggatgc ggcggccgga gcagcggcag gggcgggcct gcatacgccc tgagatctca      960
agaacgatga cctttggccg caagggtgtg agccacgggc agttctttga ccagcacctc     1020
aagtttatca agctgaacca gcagtttgtg cacttcaccc agctggacct gtcttacctg     1080
cagcgggagg cctatgaccg agattttcctc gcccgcgtct acggtgctcc ccagctgcag     1140
gtggagaaag tgaggaccaa tgaccggaag gagctggggg aggtgcgggt gcagtatacg     1200
ggcagggaca gcttcaaggc tttcgccaag gctctgggtg tcatggatga ccttaagtcg     1260
ggggttccga gagctggcta ccggggtatt gtcaccttcc agttccgggg ccgccgtgtc     1320
cacctggcgc ccccactgac gtgggagggc tatgatccta gctggaatta gcacctgcct     1380
gtccttc                                                              1387

<210> SEQ ID NO 3
<211> LENGTH: 916
<212> TYPE: DNA
<213> ORGANISM: Homo sapiens
<220> FEATURE:
<221> NAME/KEY: misc_feature
<223> OTHER INFORMATION: UDP-GlcNAc transporter

<400> SEQUENCE: 3
atgttcgcca acctaaaata cgtttccctg ggaattttgg tctttcagac taccagtttg       60
gttctaacaa tgcgttattc cagaacttta aaagaagaag acctcgtta tctatcttct       120 acagcagtgg ttgttgctga acttttgaag ataatggcct gcatttttatt ggtctacaaa      180 gacagcaaat gtagtctaag agcactgaat cgagtactac atgatgaaat tcttaataaa      240
cctatggaaa cacttaaact tgctattcca tcagggatct atactcttca gaataattta      300
ctgtatgtgg cactatcaaa tctagatgca gctacttatc aggtcacgta tcagttgaaa      360
attcttacaa cagcattatt ttctgtgtct atgcttagta aaaaattggg tgtataccag      420
tggctgtccc tagtaatttt gatgacagga gttgcttttg tacagtggcc ctcagattct      480
cagcttgatt ctaaggaact ttcagctggt tctcaatttg taggactcat ggcagttctc      540
acagcatgtt tttcaagtgg ctttgctggg gtttactttg agaaaatctt aaaagaaaca      600
aaacaatcag tgtggataag aaatattcag cttggtttct ttggaagtat atttggatta      660
atgggtgtat acattatga tggagaactg gtatcaaaga tggatttttt tcagggatat      720
aaccgactga cctggatagt agttgttctt caggcacttg gaggccttgt aatagctgct      780
gttattaagt atgcagataa tattttaaaa ggatttgcaa cctctttatc gataatatta      840
tcaacattga tctcctattt ttggcttcaa gattttgtgc caaccagtgt cttttttcctt      900 ggagccatcc ttgtaa                                                      916

<210> SEQ ID NO 4
<211> LENGTH: 3453
<212> TYPE: DNA
<213> ORGANISM: Mus musculus
<220> FEATURE:
<221> NAME/KEY: misc_feature
<223> OTHER INFORMATION: Mannosidase II

<400> SEQUENCE: 4
atgaagttaa gtcgccagtt caccgtgttt ggcagcgcga tcttctgcgt cgtaatcttc       60
tcactctacc tgatgctgga caggggtcac ttggactacc ctcggggccc gcgccaggag      120
```

```
ggctcctttc cgcagggcca gctttcaata ttgcaagaaa agattgacca tttggagcgt    180
ttgctcgctg agaacaacga gatcatctca aatatcagag actcagtcat caacctgagc    240
gagtctgtgg aggacggccc gcggggtca ccaggcaacg ccagccaagg ctccatccac    300
ctccactcgc cacagttggc cctgcaggct gaccccagag actgtttgtt tgcttcacag    360
agtgggagtc agccccggga tgtgcagatg ttggatgttt acgatctgat tccttttgat    420
aatccagatg gtggagtttg gaagcaagga tttgacatta agtatgaagc ggatgagtgg    480
gaccatgagc ccctgcaagt gtttgtggtg cctcactccc ataatgaccc aggttggttg    540
aagactttca atgactactt tagagacaag actcagtata tttttaataa catggtccta    600
aagctgaaag aagactcaag caggaagttt atgtggtctg agatctctta ccttgcaaaa    660
tggtgggata ttatagatat tccgaagaag gaagctgtta aaagtttact acagaatggt    720
cagctggaaa ttgtgaccgg tggctgggtt atgcctgatg aagccactcc acattatttt    780
gccttaattg accaactaat tgaagggcac caatggctgg aaaaaaatct aggagtgaaa    840
cctcgatcgg gctgggccat agatcccttt ggtcattcac ccacaatggc ttatcttcta    900
aagcgtgctg gattttcaca catgctcatc cagagagtcc attatgcaat caaaaaacac    960
ttctctttgc ataaaacgct ggagtttttc tggagacaga attgggatct ggatctgct    1020 acagacattt tgtgccatat gatgcccttc tacagctacg catccctca cacctgtggg   1080 cctgatccta aaatatgctg ccagtttgat tttaaacggc ttcctggagg cagatatggt   1140
tgtccctggg gagttccccc agaagcaata tctcctggaa atgtccaaag cagggctcag   1200
atgctattgg atcagtaccg gaaaagtca aacttttcc gcactaaagt tctgctggct   1260
ccactgggag acgactttcg gttcagtgaa tacacagagt gggatctgca gtgcaggaac   1320
tacgagcaac tgttcagtta catgaactcg cagcctcatc tgaaagtgaa gatccagttt   1380
ggaaccttgt cagattattt cgacgcattg gagaaagcgg tggcagccga aagaagagt   1440 agccagtctg tgttccctgc cctgagtgga gacttcttca cgtacgctga cagagacgac   1500
cattactgga gtggctactt cacgtccaga cctttctaca acgaatggga cagaataatg   1560
gaatctcgta agggctgc tgaaattctt taccagttgg ccttgaaaca agctcagaaa   1620
tacaagataa ataaatttct ttcatcacct cattacacaa cactgacaga gccagaagg   1680 aacttaggac tatttcagca tcatgatgcc atcacaggaa ccgcgaaaga ctgggtggtt   1740
gtggactatg gtaccagact ctttcagtca ttaaattctt tggagaagat aattggagat   1800
tctgcatttc ttctcatttt aaaggacaaa aagctgtacc agtcagatcc ttccaaagcc   1860
ttcttagaga tggatacgaa gcaaagttca caagattctc tgccccaaaa aattataata   1920
caactgagcg cacaggagcc aaggtacctt gtggtctaca atcccttga caagaacgg    1980 cattcagtgg tgtccatccg ggtaaactcc gccacaggga agtgctgtc tgattcggga   2040 aaaccggtgg aggttcaagt cagtgcagtt tggaacgaca tgaggacaat ttcacaagca   2100
gcctatgagg tttcttttct agctcatata ccaccactgg gactgaaagt gtttaagatc   2160
ttagagtcac aaagttcaag ctcacacttg gctgattatg tcctatataa taatgatgga   2220
ctagcagaaa atggaatatt ccacgtgaag aacatggtgg atgctggaga tgccataaca   2280
atagagaatc ccttcctggc gatttggttt gaccgatctg ggctgatgga gaaagtgaga   2340
aggaaagaag acagtagaca gcatgaactg aaggtccagt tcctgtggta cggaaccacc   2400
aacaaaaggg caagagcgg tgcctacctc ttcctgcctg acgggcaggg ccagccatat   2460
gtttccctaa gaccgcccct tgtcagagtg acacgtggaa ggatctactc agatgtgacc   2520
```

| | |
|---|---|
| tgtttcctcg aacacgttac tcacaaagtc cgcctgtaca acattcaggg aatagaaggt | 2580 |
| cagtccatgg aagtttctaa tattgtaaac atcaggaatg tgcataaccg tgagattgta | 2640 |
| atgagaattt catctaaaat aaacaaccaa aatagatatt atactgacct aaatggatat | 2700 |
| cagattcagc ctagaaggac catgagcaaa ttgcctcttc aagccaacgt ttacccgatg | 2760 |
| tgcacaatgg cgtatatcca ggatgctgag caccggctca cgctgctctc tgctcagtct | 2820 |
| ctaggtgctt ccagcatggc ttctggtcag attgaagtct tcatggatcg aaggctcatg | 2880 |
| caggatgata accgtggcct tgggcaaggc gtccatgaca ataagattac agctaatttg | 2940 |
| tttcgaatcc tcctcgagaa gagaagcgct gtgaacatgg aagaagaaaa gaagagccct | 3000 |
| gtcagctacc cttccctcct cagccacatg acttcgtcct tcctcaacca tcccttctc | 3060 |
| cccatggtac taagtggcca gctcccctcc cctgcctttg agctgctgag tgaatttcct | 3120 |
| ctgctgcagt cctctctacc ttgtgatatc catctggtca acctgcggac aatacaatca | 3180 |
| aagatgggca aaggctattc ggatgaggca gccttgatcc tccacaggaa agggtttgat | 3240 |
| tgccagttct ccagcagagg catcgggcta ccctgttcca ctactcaggg aaagatgtca | 3300 |
| gttctgaaac ttttcaacaa gtttgctgtg gagagtctcg tcccttcctc tctgtccttg | 3360 |
| atgcactccc ctccagatgc ccagaacatg agtgaagtca gcctgagccc catggagatc | 3420 |
| agcacgttcc gtatccgctt gcgttggacc tga | 3453 |

<210> SEQ ID NO 5
<211> LENGTH: 1344
<212> TYPE: DNA
<213> ORGANISM: Homo sapiens
<220> FEATURE:
<221> NAME/KEY: misc_feature
<223> OTHER INFORMATION: N-acetyl-glucosaminyl transferase II

<400> SEQUENCE: 5

| | |
|---|---|
| atgaggttcc gcatctacaa acggaaggtg ctaatcctga cgctcgtggt ggccgcctgc | 60 |
| ggcttcgtcc tctggagcag caatgggcga caaaggaaga acgaggccct cgccccaccg | 120 |
| ttgctggacg ccgaacccgc gcggggtgcc ggcggccgcg gtggggacca cccctctgtg | 180 |
| gctgtgggca tccgcagggt ctccaacgtg tcggcggctt ccctggtccc ggcggtcccc | 240 |
| cagccccgag cggacaacct gacgctgcgg taccggtccc tggtgtacca gctgaacttt | 300 |
| gatcagaccc tgaggaatgt agataaggct ggcacctggg cccccgggga gctggtgctg | 360 |
| gtggtccagg tgcataaccg gcccgaatac ctcagactgc tgctggactc acttcgaaaa | 420 |
| gcccagggaa ttgacaacgt cctcgtcatc tttagccatg acttctggtc gaccgagatc | 480 |
| aatcagctga tcgccggggt gaatttctgt ccggttctgc aggtgttctt cctttcagc | 540 |
| attcagttgt accctaacga gttccaggt agtgaccta gagattgtcc cagagacctg | 600 |
| ccgaagaatg ccgctttgaa attggggtgc atcaatgctg agtatcccga ctccttcggc | 660 |
| cattatagag aggccaaatt ctcccagacc aaacatcact ggtggtggaa gctgcatttt | 720 |
| gtgtgggaaa gagtgaaaat tcttcgagat tatgctggcc ttatactttt cctagaagag | 780 |
| gatcactact tagccccaga cttttaccat gtcttcaaaa agatgtggaa actgaagcag | 840 |
| caagagtgcc ctgaatgtga tgttctctcc tggggaccta tagtgccag tcgcagtttc | 900 |
| tatggcatgg ctgacaaggt agatgtgaaa acttggaaat ccacagagca caatatgggt | 960 |
| ctagccttga cccggaatgc ctatcagaag ctgatcgagt gcacagacac tttctgtact | 1020 |
| tatgatgatt ataactggga ctggactctt caatacttga ctgtatcttg tcttccaaaa | 1080 |

```
ttctggaaag tgctggttcc tcaaattcct aggatctttc atgctggaga ctgtggtatg    1140
catcacaaga aaacctgtag accatccact cagagtgccc aaattgagtc actcttaaat    1200
aataacaaac aatacatgtt tccagaaact ctaactatca gtgaaaagtt tactgtggta    1260
gccatttccc cacctagaaa aaatggaggg tggggagata ttagggacca tgaactctgt    1320
aaaagttata gaagactgca gtga                                           1344
```

<210> SEQ ID NO 6
<211> LENGTH: 1047
<212> TYPE: DNA
<213> ORGANISM: Artificial Sequence
<220> FEATURE:
<223> OTHER INFORMATION: Galactosyl transferase I lacking the human
      targeting sequence

<400> SEQUENCE: 6

```
ccccaactgg tcggagtctc cacaccgctg cagggcggct cgaacagtgc cgccgccatc      60
gggcagtcct ccggggagct ccggaccgga ggggcccggc cgccgcctcc tctaggcgcc     120
tcctcccagc cgcgcccggg tggcgactcc agcccagtcg tggattctgg ccctggcccc     180
gctagcaact tgacctcggt cccagtgccc cacaccaccg cactgtcgct gcccgccctgc    240 cctgaggagt ccccgctgct tgtgggcccc atgctgattg agtttaacat gcctgtggac    300
ctggagctcg tggcaaagca gaacccaaat gtgaagatgg gcggccgcta tgcccccagg    360
gactgcgtct ctcctcacaa ggtggccatc atcattccat tccgcaaccg gcaggagcac    420
ctcaagtact ggctatatta tttgcaccca gtcctgcagc gccagcagct ggactatggc    480
atctatgtta tcaaccaggc gggagacact atattcaatc gtgctaagct cctcaatgtt    540
ggctttcaag aagccttgaa ggactatgac tacacctgct ttgtgtttag tgacgtggac    600
ctcattccaa tgaatgacca taatgcgtac aggtgttttt cacagccacg gcacatttcc    660
gttgcaatgg ataagtttgg attcagccta ccttatgttc agtattttgg aggtgtctct    720
gctctaagta acaacagtt tctaaccatc aatggatttc ctaataatta ttggggctgg    780
ggaggagaag atgatgacat ttttaacaga ttagttttta gaggcatgtc tatatctcgc    840
ccaaatgctg tggtcgggag gtgtcgcatg atccgccact caagagacaa gaaaaatgaa    900
cccaatcctc agaggtttga ccgaattgca cacacaaagg agacaatgct ctctgatggt    960
ttgaactcac tcacctacca ggtgctggat gtacagagat acccattgta tacccaaatc   1020
acagtggaca tcgggacacc gagctag                                       1047
```

<210> SEQ ID NO 7
<211> LENGTH: 1801
<212> TYPE: DNA
<213> ORGANISM: Homo sapiens
<220> FEATURE:
<221> NAME/KEY: misc_feature
<223> OTHER INFORMATION: alpha-1,6-fucosyltransferase FUT8

<400> SEQUENCE: 7

```
caggactcca gggaagtgag ttgaaaatct gaaaatgcgg ccatggactg gttcctggcg     60
ttggattatg ctcattcttt ttgcctgggg gaccttgctg ttttatatag gtggtcactt    120
ggtacgagat aatgaccatc ctgatcactc tagccgagaa ctgtccaaga ttctggcaaa    180
gcttgaacgc ttaaaacagc agaatgaaga cttgaggcga atggccgaat ctctccggat    240
accagaaggc cctattgatc aggggccagc tataggaaga gtacgcgttt tagaagagca    300
gcttgttaag gccaaagaac agattgaaaa ttacaagaaa cagaccagaa atggtctggg    360
```

```
gaaggatcat gaaatcctga ggaggaggat tgaaaatgga gctaaagagc tctggttttt      420
cctacagagt gaattgaaga aattaaagaa cttagaagga aatgaactcc aaagacatgc      480
agatgaattt cttttggatt taggacatca tgaaaggtct ataatgacgg atctatacta      540
cctcagtcag acagatggag caggtgattg gcgggaaaaa gaggccaaag atctgacaga      600
actggttcag cggagaataa catatcttca gaatcccaag gactgcagca aagccaaaaa      660
gctggtgtgt aatatcaaca aaggctgtgg ctatggctgt cagctccatc atgtggtcta      720
ctgcttcatg attgcatatg gcacccagcg aacactcatc ttggaatctc agaattggcg      780
ctatgctact ggtggatggg agactgtatt taggcctgta agtgagacat gcacagacag      840
atctggcatc tccactggac actggtcagg tgaagtgaag acaaaaatg ttcaagtggt       900 cgagcttccc attgtagaca gtcttcatcc ccgtcctcca tatttaccct ggctgtacc      960 agaagacctc gcagatcgac ttgtacgagt gcatggtgac cctgcagtgt ggtgggtgtc    1020
tcagtttgtc aaatacttga tccgcccaca gccttggcta gaaaaagaaa tagaagaagc    1080
caccaagaag cttggcttca acatccagt tattggagtc catgtcagac gcacagacaa     1140
agtgggaaca gaagctgcct tccatcccat tgaagagtac atggtgcatg ttgaagaaca    1200
ttttcagctt cttgcacgca gaatgcaagt ggacaaaaaa agagtgtatt tggccacaga    1260
tgacccttct ttattaaagg aggcaaaaac aaagtacccc aattatgaat ttattagtga    1320
taactctatt tcctggtcag ctggactgca caatcgatac acagaaaatt cacttcgtgg    1380
agtgatcctg gatatacatt ttctctctca ggcagacttc ctagtgtgta ctttttcatc    1440
ccaggtctgt cgagttgctt atgaaattat gcaaacacta catcctgatg cctctgcaaa    1500
cttccattct ttagatgaca tctactattt tgggggccag aatgcccaca atcaaattgc    1560
catttatgct caccaacccc gaactgcaga tgaaattccc atggaacctg agatatcat    1620 tggtgtggct ggaaatcatt gggatggcta ttctaaaggt gtcaacagga aattgggaag    1680
gacgggccta tatccctcct acaaagttcg agagaagata gaaacggtca gtacccac     1740 atatcctgag gctgagaaat aaagctcaga tggaagagat aaacgaccaa actcagttcg    1800
a                                                                    1801
```

<210> SEQ ID NO 8
<211> LENGTH: 1136
<212> TYPE: DNA
<213> ORGANISM: Homo sapiens
<220> FEATURE:
<221> NAME/KEY: misc_feature
<223> OTHER INFORMATION: GDP-fucose transporter

<400> SEQUENCE: 8

```
tgacccagct cctctgctac catgaatagg gcccctctga agcggtccag gatcctgcac       60
atggcgctga ccggggcctc agaccccctct gcagaggcag aggccaacgg ggagaagccc     120
tttctgctgc gggcattgca gatcgcgctg gtggtctccc tctactgggt cacctccatc      180
tccatggtgt tccttaataa gtacctgctg gacagcccct ccctgcggct ggacaccccc      240
atcttcgtca ccttctacca gtgcctggtg accacgctgc tgtgcaaagg cctcagcgct      300
ctggccgcct gctgcctgg tgccgtggac ttccccagct gcgcctgga cctcagggtg       360 gcccgcagcg tcctgcccct gtcggtggtc ttcatcggca tgatcacctt caataacctc      420
tgcctcaagt acgtcggtgt ggccttctac aatgtgggcc gctcactcac caccgtcttc      480
aacgtgctgc tctcctacct gctgctcaag cagaccacct ccttctatgc cctgctcacc      540
tgcggtatca tcatcggggg cttctggctt ggtgtggacc aggagggggc agaaggcacc      600
```

```
ctgtcgtggc tgggcaccgt cttcggcgtg ctggctagcc tctgtgtctc gctcaacgcc    660
atctacacca cgaaggtgct cccggcgtgt gacggcagca tctggcgcct gactttctac    720
aacaacgtca acgcctgcat cctcttcctg cccctgctcc tgctgctcgg ggagcttcag    780
gccctgcgtg actttgccca gctgggcagt gcccacttct ggggatgat gacgctgggc     840 ggcctgtttg gctttgccat cggctacgtg acaggactgc agatcaagtt caccagtccg    900
ctgacccaca atgtgtcggg cacggccaag gcctgtgccc agacagtgct ggccgtgctc    960
tactacgagg agaccaagag cttcctctgg tggacgagca acatgatggt gctgggcggc    1020
tcctccgcct acacctgggt cagggctgg gagatgaaga agactccgga ggagcccagc    1080
cccaaagaca gcgagaagag cgccatgggg gtgtgagcac cacaggcacc ctggat       1136
```

<210> SEQ ID NO 9
<211> LENGTH: 268
<212> TYPE: DNA
<213> ORGANISM: herpes simplex virus
<220> FEATURE:
<221> NAME/KEY: misc_feature
<223> OTHER INFORMATION: Thymidine kinase promoter

<400> SEQUENCE: 9

```
gcagtgtggt tttgcaagag gaagcaaaaa gcctctccac ccaggcctgg aatgtttcca    60
cccaatgtcg agcagtgtgg ttttgcaaga ggaagcaaaa agcctctcca cccaggcctg    120
gaatgtttcc acccaatgtc gagcaaaccc cgcccagcgt cttgtcattg gcgaattcga    180
acacgcagat gcagtcgggg cggcgcggtc ccaggtccac ttcgcatatt aaggtgacgc    240
gtgtggcctc gaacaccgag cgaccctg                                      268
```

<210> SEQ ID NO 10
<211> LENGTH: 990
<212> TYPE: DNA
<213> ORGANISM: Homo sapiens
<220> FEATURE:
<221> NAME/KEY: misc_feature
<223> OTHER INFORMATION: Sialyltransferase (NM_006278)

<400> SEQUENCE: 10

```
atggtcagca gtcccgctg gaagctcctg gccatgttgg ctctggtcct ggtcgtcatg     60
gtgtggtatt ccatctcccg ggaagacagt ttttattttc ccatcccaga gaagaaggag    120
ccgtgcctcc agggtgaggc agagagcaag gcctctaagc tctttggcaa ctactcccgg    180
gatcagccca tcttcctgcg gcttgaggat tatttctggg tcaagacgcc atctgcttac    240
gagctgccct atgggaccaa ggggagtgag gatctgctcc tccgggtgct agccatcacc    300
agctcctcca tccccaagaa catccagagc ctcaggtgcc gccgctgtgt ggtcgtgggg    360
aacgggcacc ggctgcggaa cagctcactg ggagatgcca tcaacaagta cgatgtggtc    420
atcagattga caatgccccc agtggctggc tatgagggtg acgtgggctc caagaccacc    480
atgcgtctct ctctaccctga atctgcccac ttcgacccca agtagaaaaa caacccagac    540
acactcctcg tcctggtagc tttcaaggca atggacttcc actggattga accatcctg     600 agtgataaga gcgggtgcg aaagggtttc tggaacagc ctcccctcat ctgggatgtc     660
aatcctaaac agattcggat tctcaacccc ttcttcatgg agattgcagc tgacaaactg    720
ctgagcctgc caatgcaaca gccacggaag attaagcaga gcccaccac gggcctgttg    780 gccatcacgc tggccctcca cctctgtgac ttggtgcaca ttgccggctt tggctaccca    840
gacgcctaca acaagaagca gaccattcac tactatgagc agatcacgct caagtccatg    900
```

```
gcggggtcag gccataatgt ctcccaagag gccctggcca ttaagcggat gctggagatg    960
ggagctatca agaacctcac gtccttctga                                    990
```

<210> SEQ ID NO 11
<211> LENGTH: 681
<212> TYPE: DNA
<213> ORGANISM: Artificial Sequence
<220> FEATURE:
<223> OTHER INFORMATION: EPO modified sequence

<400> SEQUENCE: 11

```
atgggggtgc acgaatgtcc tgcctggctg tggcttctcc tgtccctgct gtcgctccct     60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctggga    420
gcccagaagg aagccatctc ccctccagat gcagcctcag ctgctccgct ccgaacaatc    480
actgctgaca ctttccgcaa actcttccga gtctactcca tttcctccg ggaaagctg     540 aagctgtaca gggggaggc ctgcaggaca ggcgacagaa agggcgagct tcgaggtcac    600
ccattcgaag gtaagcctat ccctaaccct ctcctcggtc tcgattctac gcgtaccggt    660
catcatcacc atcaccattg a                                             681
```

<210> SEQ ID NO 12
<211> LENGTH: 225
<212> TYPE: PRT
<213> ORGANISM: Artificial Sequence
<220> FEATURE:
<223> OTHER INFORMATION: EPO sequenced in the expression plasmid

<400> SEQUENCE: 12

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Gln Leu His Val Asp Lys Ala Val Ser Gly Leu
        115                 120                 125

Arg Ser Leu Thr Thr Leu Leu Arg Ala Leu Gly Ala Gln Lys Glu Ala
    130                 135                 140

Ile Ser Pro Pro Asp Ala Ala Ser Ala Ala Pro Leu Arg Thr Ile Thr
145                 150                 155                 160

Ala Asp Thr Phe Arg Lys Leu Phe Arg Val Tyr Ser Asn Phe Leu Arg
```

```
                   165                 170                 175
Gly Lys Leu Lys Leu Tyr Thr Gly Glu Ala Cys Arg Thr Gly Asp Arg
            180                 185                 190

Lys Gly Glu Leu Arg Gly His Pro Phe Glu Gly Lys Pro Ile Pro Asn
        195                 200                 205

Pro Leu Leu Gly Leu Asp Ser Thr Arg Thr Gly His His His His
    210                 215                 220

His
225

<210> SEQ ID NO 13
<211> LENGTH: 51
<212> TYPE: DNA
<213> ORGANISM: Artificial Sequence
<220> FEATURE:
<223> OTHER INFORMATION: Mmn9 cytoplasmic domain

<400> SEQUENCE: 13
atgtcacttt ctcttgtatc gtaccgccta agaaagaacc cgtgggttaa c            51

<210> SEQ ID NO 14
<211> LENGTH: 246
<212> TYPE: DNA
<213> ORGANISM: Saccharomyces cerevisiae

<400> SEQUENCE: 14
atggccctct ttctcagtaa gagactgttg agatttaccg tcattgcagg tgcggttatt    60
gttctcctcc taacattgaa ttccaacagt agaactcagc aatatattcc gagttccatc   120
tccgctgcat ttgattttac ctcaggatct atatcccctg aacaacaagt catctctgag   180
gaaaatgatg ctaaaaaatt agagcaaagt gctctgaatt cagaggcaag cgaagactcc   240
gaagcc                                                              246

<210> SEQ ID NO 15
<211> LENGTH: 274
<212> TYPE: DNA
<213> ORGANISM: Artificial Sequence
<220> FEATURE:
<223> OTHER INFORMATION: CYC1 terminator only

<400> SEQUENCE: 15
gaattggtcg atcaggtatt catgtaatta gttatgtcac gcttacattc acgccctccc    60
cccacatccg ctctaaccga aaaggaagga gttagacaac ctgaagtcta ggtccctatt   120 tatttttta tagttatgtt agtattaaga acgttattta tatttcaaat ttttcttttt   180
tttctgtaca gacgcgtgta cgcatgtaac attatactga aaaccttgct tgagaaggtt   240
ttgggacgct cgaaggcttt aatttgcaag ctgc                               274

<210> SEQ ID NO 16
<211> LENGTH: 679
<212> TYPE: DNA
<213> ORGANISM: Saccharomyces cerevisiae
<220> FEATURE:
<221> NAME/KEY: misc_feature
<223> OTHER INFORMATION: pGAP promoter

<400> SEQUENCE: 16
tcgagtttat cattatcaat actcgccatt tcaagaaata cgtaaataat taatagtagt    60
gattttccta actttattta gtcaaaaaat tagccttta attctgctgt aacccgtaca   120
tgccaaaata gggggcgggt tacacagaat atataacact gatggtgctt gggtgaacag   180
```

```
gtttattcct ggcatccact aaatataatg gagcccgctt tttaagctgg catccagaaa       240
aaaaaagaat cccagcacca aaatattgtt ttcttcacca accatcagtt cataggtcca       300
ttctcttagc gcaactacag agaacagggc acaaacaggc aaaaaacggg cacaacctca       360
atggagtgat gcaacctgcc tggagtaaat gatgacacaa ggcaattgac ccacgcatgt       420
atctatctca ttttcttaca ccttctatta ccttctgctc tctctgattt ggaaaaagct       480
gaaaaaaaag gttgaaacca gttccctgaa attattcccc tacttgacta ataagtatat       540
aaagacggta ggtattgatt gtaattctgt aaatctattt cttaaacttc ttaaattcta       600
cttttatagt tagtcttttt tttagtttta aaacaccaag aacttagttt cgaataaaca       660
cacataaata aacaaaatg                                                    679

<210> SEQ ID NO 17
<211> LENGTH: 451
<212> TYPE: DNA
<213> ORGANISM: Saccharomyces cerevisiae
<220> FEATURE:
<221> NAME/KEY: misc_feature
<223> OTHER INFORMATION: pGAL1 promoter

<400> SEQUENCE: 17
acggattaga agccgccgag cgggtgacag ccctccgaag gaagactctc ctccgtgcgt        60
cctcgtcttc accggtcgcg ttcctgaaac gcagatgtgc ctcgcgccgc actgctccga       120
acaataaaga ttctacaata ctagctttta tggttatgaa gaggaaaaat tggcagtaac       180
ctggccccac aaaccttcaa atgaacgaat caaattaaca accataggat gataatgcga       240
ttagtttttt agccttattt ctggggtaat taatcagcga agcgatgatt tttgatctat       300
taacagatat ataaatgcaa aaactgcata accactttaa ctaatacttt caacattttc       360
ggtttgtatt acttcttatt caatgtaat aaaagtatca acaaaaaatt gttaatatac       420
ctctatactt taacgtcaag gagaaaaaac c                                      451

<210> SEQ ID NO 18
<211> LENGTH: 603
<212> TYPE: DNA
<213> ORGANISM: Saccharomyces cerevisiae
<220> FEATURE:
<221> NAME/KEY: misc_feature
<223> OTHER INFORMATION: PGK promoter

<400> SEQUENCE: 18
cccaagctta cctgctgcgc attgttttat atttgttgta aaaagtagat aattacttcc        60
ttgatgatct gtaaaaaaga gaaaagaaa gcatctaaga acttgaaaaa ctacgaatta       120
gaaaagacca aatatgtatt tcttgcattg accaatttat gcaagtttat atatatgtaa       180
atgtaagttt cacgaggttc tactaaacta accacccccc ttggttagaa gaaaagagtg       240
tgtgagaaca ggctgttgtt gtcacacgat tcggacaatt ctgtttgaaa gagagagagt       300
aacagtacga tcgaacgaac tttgctctgg agatcacagt gggcatcata gcatgtggta       360
ctaaaccctt tcccgccatt ccagaacctt cgattgcttg ttacaaaacc tgtgagccgt       420
cgctaggacc ttgttgtgtg acgaaattgg aagctgcaat caataggaag acaggaagtc       480
gagcgtgtct gggttttttc agtttgttc ttttgcaaa caaatcacga gcgacggtaa       540
tttctttctc gataagaggc cacgtgcttt atgagggtaa catcaattca agatctgaat       600
tcc                                                                    603
```

```
<210> SEQ ID NO 19
<211> LENGTH: 409
<212> TYPE: DNA
<213> ORGANISM: Saccharomyces cerevisiae
<220> FEATURE:
<221> NAME/KEY: misc_feature
<223> OTHER INFORMATION: TEF promoter

<400> SEQUENCE: 19
cccacacacc atagcttcaa aatgtttcta ctccttttt actcttccag attttctcgg      60
actccgcgca tcgccgtacc acttcaaaac acccaagcac agcatactaa attttccctc    120
tttcttcctc tagggtgtcg ttaattaccc gtactaaagg tttggaaaag aaaaaagaga    180
ccgcctcgtt tcttttcttt cgtcgaaaaa ggcaataaaa attttatca cgtttctttt     240 tcttgaaatt tttttttta gttttttct ctttcagtga cctccattga tatttaagtt     300
aataaacggt cttcaatttc tcaagtttca gtttcatttt tcttgttcta ttacaacttt    360
ttttacttct tgttcattag aaagaaagca tagcaatcta atctaaggg                409

<210> SEQ ID NO 20
<211> LENGTH: 936
<212> TYPE: DNA
<213> ORGANISM: Saccharomyces cerevisiae
<220> FEATURE:
<221> NAME/KEY: misc_feature
<223> OTHER INFORMATION: PMA1 promoter

<400> SEQUENCE: 20
aagcttcctg aaacggagaa acataaacag gcattgctgg gatcacccat acatcactct     60
gttttgcctg acctttccg gtaatttgaa acaaacccg gtctcgaagc ggagatccgg     120
cgataattac cgcagaaata aacccataca cgagacgtag aaccagccgc acatggccgg   180
agaaactcct gcgagaattt cgtaaactcg cgcgcattgc atctgtattt cctaatgcgg    240
cacttccagg cctcgagacc tctgacatgc ttttgacagg aatagacatt ttcagaatgt   300
tatccatatg cctttcgggt ttttttcctt cctttccat catgaaaaat ctctcgagac    360
cgtttatcca ttgctttttt gttgtctttt tccctcgttc acagaaagtc tgaagaagct    420
atagtagaac tatgagcttt ttttgtttct gttttcctt tttttttt tacctctgtg     480 gaaattgtta ctctcacact ctttagttcg tttgtttgtt ttgttattc caattatgac    540 cggtgacgaa acgtggtcga tggtgggtac cgcttatgct cccctccatt agtttcgatt   600
atataaaaag gccaaatatt gtattatttt caaatgtcct atcattatcg tctaacatct    660
aatttctctt aaatttttc tctttctttc ctataacacc aatagtgaaa atctttttt     720 cttctatatc tacaaaaact ttttttttct atcaacctcg ttgataaatt ttttctttaa    780
caatcgttaa taattaatta attggaaaat aaccattttt tctctctttt atacacacat   840
tcaaaagaaa gaaaaaaaat atccccagc tagttaaaga aaatcattga aaagaataag   900
aagataagaa agatttaatt atcaaacaat atcaat                              936

<210> SEQ ID NO 21
<211> LENGTH: 504
<212> TYPE: DNA
<213> ORGANISM: Cauliflower mosaic virus

<400> SEQUENCE: 21
caacagaact cgccgtgaag actggcgaac agttcataca gagtctttta cgactcaatg     60
acaagaagaa aatcttcgtc aacatggtgg agcacgacac tctggtctac tccaaaaatg   120
tcaaagatac agtctcagaa gaccaaaggg ctattgagac ttttcaacaa aggataattt   180
```

```
cgggaaacct cctcggattc cattgcccag ctatctgtca cttcatcgaa aggacagtag    240
aaaaggaagg tggctcctac aaatgccatc attgcgataa aggaaaggct atcattcaag    300
atctgcctct gccgacagtg gtcccaaaga tggaccccca cccacgagga gcatcgtgga    360
aaaagaagac gttccaacca cgtcttcaaa gcaagtggat tgatgtgaca tctccactga    420
cgtaagggat gacgcacaat cccactatcc ttcgcaagac ccttcctcta tataaggaag    480
ttcatttcat ttggagagga cacg                                          504
```

<210> SEQ ID NO 22
<211> LENGTH: 623
<212> TYPE: DNA
<213> ORGANISM: Saccharomyces cerevisiae
<220> FEATURE:
<221> NAME/KEY: misc_feature
<223> OTHER INFORMATION: Pho5 promoter

<400> SEQUENCE: 22

```
gatccgaaag ttgtattcaa caagaatgcg caaatatgtc aacgtatttg gaagtcatct     60
tatgtgcgct gctttaatgt tttctcatgt aagcggacgt cgtctataaa cttcaaacga    120
aggtaaaagg ttcatagcgc ttttctttg tctgcacaaa gaaatatata ttaaattagc    180
acgttttcgc atagaacgca actgcacaat gccaaaaaaa gtaaagtga ttaaaagagt    240 taattgaata ggcaatctct aaatgaatcg atacaacctt ggcactcaca cgtgggacta    300
gcacagacta aatttatgat tctggtccct gttttcgaag agatcgcaca tgccaaatta    360
tcaaattggt caccttactt ggcaaggcat atacccattt gggataaggg taaacatctt    420
tgaattgtcg aaatgaaacg tatataagcg ctgatgtttt gctaagtcga ggttagtatg    480
gcttcatctc tcatgagaat aagaacaaca acaaatagag caagcaaatt cgagattacc    540
aatgtttaaa tctgttgttt attcaatttt agccgcttct ttggccaatg caggtaccat    600
tcccttaggc aaactagccg atg                                           623
```

<210> SEQ ID NO 23
<211> LENGTH: 1501
<212> TYPE: DNA
<213> ORGANISM: Saccharomyces cerevisiae
<220> FEATURE:
<221> NAME/KEY: misc_feature
<223> OTHER INFORMATION: Actin-binding protein promoter

<400> SEQUENCE: 23

```
gaattcggaa gactcagact tcccaacagg cagaaaattc agaagtcata aaggaccttt     60
acgagtacct ctgtaacgta cgtgtacata aaagctacga ggatgattct gggttgtggt    120
tcgacatctc gcagggcacc cactcagggg gatcttccga tgattattcg ataatggact    180
ataaactcgg atttgtcaag ggccaggcca agtcacagaa gtcatatatg cgcccgttct    240
taaacagcga tccaccgagg aactatactc gctacagtcg aaactaccgg aatacctctt    300
cgaaacgttg agtttccccc ctctcgtcgct aaaccaattc tataacaaaa tcgctaaaag    360
cctgaataag aaaagagaga aaaaagatga aaccgagtaa gctgctacat aatgtctata    420
tatctacaca taaaattccg attattcctt tgcatacctg atttgcccct cagaatccac    480
aaccagactt tcaagaagg tctttttgc ccctttatcc ttcatggttt tcaaattttg    540
tacaacgact tgcccttgtg aagctcgata ccgttcgagg tcttttccac tttctctgcc    600
ttcttgatca caggcttctc cactttcttt gcaggagttg ccactgctgg tgctggtgct    660
gcttctgctg ctgcttctgc tgctgcttct gcttctgctt cttgttgccc ttgtacaacg    720
```

```
ctttctggta cttctcgtcc tcgctgatgc aagacgtgtg attcttgtaa ctcacgccat      780
cttcaaacgt cttggagcaa tctatgcatg tatagtacgc gttaggacat ctataataat      840
gcttttcggt attcttcttg ggcacagtat cattgcacac ctcacagttg aacgtaacca      900
tcctgtaata acaaatattt cttgactgag accgtttgct gttgtataca gaatactctt      960
agagctcatc gcaagttaaa aattttcaat ttttttcac ttttcccgt caaggcaaaa       1020 agcaaccaaa agagaatgaa cctttatttt tgatttattt attatgagat gctgctagtc     1080
cactcatctg catcaatgta gtagtcacaa agctaatatt tagacgttac tttgatatct     1140
ctgtccatga gagcacttat tttaggaagt taaatgagac agtcaatagt tcacaatatc     1200
ccgtcagcaa tggagggaaa aggcattcct tttccatagg attttaatcg ttttcaagca     1260
tcatacgccc tcgaggaact cttgttttcg ctttactatg caaccattga tgtatttctg     1320
tataaatgtg cgtcacgtgg ccttgtgtct cttatttcca cttgtttttt cacaatgcgg     1380
aaaacctcga ttaaagtaga aaaaaaggat ataataggag tataccatat tggatagttc     1440
aatctataaa caaacaatcg cataaccgca cgtatataca cgcacacacc tatcaatcac     1500
a                                                                     1501

<210> SEQ ID NO 24
<211> LENGTH: 384
<212> TYPE: DNA
<213> ORGANISM: Saccharomyces cerevisiae
<220> FEATURE:
<221> NAME/KEY: misc_feature
<223> OTHER INFORMATION: Putative CYC1 promoter

<400> SEQUENCE: 24
cccgggagca agatcaagat gttttcaccg atctttccgg tctctttggc cggggtttac       60
ggacgatgac cgaagaccaa cgccagctc atttggcgag cgttggttgg tggatcaagc      120
ccacgcgtag gcaatcctcg agcagatccg ccaggcgtgt atatagcgtg gatggccagg     180
caactttagt gctgacacat acaggcatat atatatgtgt gcgacgacac atgatcatat     240
ggcatgcatg tgctctgtat gtatataaaa ctcttgtttt cttcttttct ctaaatattc     300
tttccttata cattaggtcc tttgtagcat aaattactat acttctatag acacgcaaac     360
acaaatacac acactaaatt aata                                            384

<210> SEQ ID NO 25
<211> LENGTH: 444
<212> TYPE: DNA
<213> ORGANISM: Schizosaccharomyces pombe
<220> FEATURE:
<221> NAME/KEY: misc_feature
<223> OTHER INFORMATION: CYC1 promoter

<400> SEQUENCE: 25
atcataccaa gaccaaccac acatgctgaa gatgcattgc atgccacgaa atcattgcat       60
atcagccaat tccagttttc caacgattac tgcactctaa cgatatctat tttccttatt     120 ttcgacacg gtatacaacc ttaattatgt ttaatacggc tgctcgtcat caccaaatcc      180 tgttttact ttaacgaagg ttatcgcacg caaaaaaggt aaacattgga ttggctcgcc      240
```

| | |
|---|---|
| atgtcattcc gcggagagct catgaaccaa tgaaataagg gcgaaaaaat aaatttaaag | 300 |
| gtcgacttcc accgcatccc aacttactct caacgtacat cttctcacta acttcgcggt | 360 |
| gaatttgtgg tttttaaatc ttcttctcta caaatactaa actcttaagc ctatttcctt | 420 |
| tccttagcaa tttattaatt caaa | 444 |

<210> SEQ ID NO 26
<211> LENGTH: 159
<212> TYPE: DNA
<213> ORGANISM: Saccharomyces cerevisiae
<220> FEATURE:
<221> NAME/KEY: misc_feature
<223> OTHER INFORMATION: ADH2 promoter

<400> SEQUENCE: 26

| | |
|---|---|
| cctatcacat ataaatagag tgccagtagc gactttttc acactcgaga tactcttact | 60 |
| actgctctct tgttgttttt atcacttctt gtttcttctt ggtaaataga atatcaagct | 120 |
| acaaaaagca tacaatcaac tatcaactat taactatat | 159 |

<210> SEQ ID NO 27
<211> LENGTH: 1617
<212> TYPE: DNA
<213> ORGANISM: Mus musculus
<220> FEATURE:
<221> NAME/KEY: misc_feature
<223> OTHER INFORMATION: beta-1,4 N-acetylglucosaminyltransferase III

<400> SEQUENCE: 27

| | |
|---|---|
| atgaagatga gacgctacaa gctctttctc atgttctgta tggctggcct gtgcctcata | 60 |
| tccttcctgc acttctttaa gaccttatcc tatgtcacct tcccgagaga actggcctcc | 120 |
| ctcagcccta acctcgtatc cagcttcttc tggaacaatg cccctgtcac tcccaggcc | 180 |
| agtccggagc cgggtggccc cgacctattg cggacacccc tctactccca ctctcccctg | 240 |
| ctccagccac tgtccccgag caaggccaca gaggaactgc accgggtgga cttcgtgttg | 300 |
| ccggaggaca ccacggagta ttttgtgcgc accaaagctg gtggtgtgtg cttcaaacca | 360 |
| ggtaccagga tgctggagaa accttcgcca gggcggacag aggagaagcc cgaagtgtct | 420 |
| gagggctcct cagcccgggg acctgctcgg aggcccatga ggcacgtgtt gagtacgcgg | 480 |
| gagcgcctgg gcagccgggg cactaggcgc aagtgggttg agtgtgtgtg cctgccaggc | 540 |
| tggcacgggc ccagttgcgg ggtgcccacg gtggtgcagt attccaacct gcccaccaag | 600 |
| gaacgcctgt acccaggga ggtaccgagg cgggttatca acgccatcaa catcaaccac | 660 |
| gagttcgacc tgctggatgt gcgtttccat gagctgggag atgttgtgga cgccttcgtg | 720 |
| gtctgtgaat ctaatttcac cgcctacggg gagcctcggc cgctcaagtt ccgagagatg | 780 |
| ctgaccaatg gcaccttcga gtacatccgc cacaaggtgc tctatgtctt cctggaccat | 840 |
| ttcccacctg gtggccgtca ggacggctgg attgcggatg actacctgcg caccttcctc | 900 |
| acccaggatg gcgtctcccg cctgcgcaac ctgcggcccg atgacgtctt tatcatcgac | 960 |
| gatgcggacg agatccctgc gcgtgatggt gtgctgttcc tcaaactcta cgatggctgg | 1020 |
| acagagccct tcgccttcca catgcggaag tccctgtatg gtttcttctg gaagcagccg | 1080 |
| ggcacactgg aggtggtgtc aggctgcacc atggacatgc tgcaggccgt gtatgggctg | 1140 |
| gatggcatcc gcctgcgccg ccgccagtac tacaccatgc ccaacttccg gcagtatgag | 1200 |
| aaccgcaccg gccacatcct agtgcagtgg tctctcggca gcccccctgca cttcgcgggc | 1260 |
| tggcattgct cctggtgctt cacacccgag ggcatctact ttaaactcgt gtcagcccag | 1320 |

```
aatggcgact tcccccgctg gggtgactat gaggacaaga gggacctcaa ttacatccgc    1380
agcttgatcc gcactggggg atggttcgac ggaacgcagc aggagtaccc tcctgcggac    1440
cccagtgagc acatgtatgc tcctaaatac ctgctcaaga actatgacca gttccgctac    1500
ttgctggaaa atccctaccg ggagcccaag agcactgaag agggtgggcg ccggaaccag    1560
ggctcagatg gaaggccatc tgctgtcagg ggcaagttgg atacagtgga gggctag      1617
```

The invention claimed is:

1. Genetically modified yeast cells, capable of producing glycoproteins having homogeneous glycans comprising the Man5GlcNac2 structure, said yeast cells comprising the following modifications:
   a) inactivation of the Och1 gene coding for α1,6-mannosyl transferase by insertion by homologous recombination of a heterologous sequence coding for a gene of resistance to an antibiotic (delta-Och1 strain);
   b) integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for an α-1-2 mannosidase I comprising a targeting sequence in the endoplasmic reticulum or Golgi apparatus and a terminator of the transcription; and
   c) integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, said promoter in c) being different from the promoter in b), an open reading phase comprising the sequence coding for an exogenous glycoprotein to be produced and a terminator of the transcription,
   wherein the yeast cells are Saccharomyces cerevisiae or Schizosaccharomyces pombe.

2. The yeast cells according to claim 1, wherein α-1-2 mannosidase I is the α-1-2 mannosidase I of C. Elegans encoded by a DNA sequence comprising SEQ ID NO 1.

3. The yeast cells according to claim 1, capable of producing glycoproteins having more than 75% of the GlcNacMan5GlcNac2 structure, further comprising the integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for human N-acetyl-glucosaminyl transferase I comprising a targeting sequence in the endoplasmic reticulum or Golgi apparatus or a terminator of the transcription.

4. The yeast cells according to claim 3, wherein the human N-acetyl-glucosaminyl transferase I comprises the sequence SEQ ID NO 2 without the cytoplasmic portion of the enzyme which is replaced with the cytoplasmic portion of mmn9 (SEQ ID NO 13) for Golgi localization of the protein.

5. The yeast cells according to claim 4, further comprising the integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for the human UDP-GlcNAc transporter and a terminator of the transcription.

6. The yeast cells according to claim 5, wherein the human UDP-GlcNAc transporter comprises the sequence SEQ ID NO 3.

7. The yeast cells according to claim 4, capable of producing glycoproteins having more than 75% of the GlcNacMan3GlcNac2 structure, further comprising an integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for a mannosidase II comprising a targeting sequence in the endoplasmic reticulum or Golgi apparatus and a terminator of the transcription.

8. The yeast cells according to claim 7, wherein the mannosidase II is murine mannosidase II and comprises the sequence SEQ ID NO 4.

9. The yeast cells according to claim 7, capable of producing glycoproteins having more than 75% of the GlcNac4Man3GlcNac2 structure, further comprising an integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for an N-acetyl-glucosaminyl transferase II, comprising a targeting sequence in the endoplasmic reticulum or Golgi apparatus and a terminator of the transcription.

10. The yeast cells according to claim 9, wherein the N-acetyl-glucosaminyl transferase II is human and comprises the sequence SEQ ID NO 5.

11. The yeast cells according to claim 9, capable of producing glycoproteins having more than 75% of the Gal4GlcNac4Man3GlcNac2 structure, further comprising an integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, an open reading phase comprising the sequence coding for a galactosyl transferase I, comprising a targeted sequence in the endoplasmic reticulum or Golgi apparatus and a terminator of the transcription.

12. The yeast cells according to claim 11, wherein the galactosyl transferase I is human, and comprises the sequence SEQ ID NO 6, which is without the human targeting sequence.

13. The yeast cells according to claim 1, wherein the integration marker is selected from URA3, ADE2, LYS2, LEU2, TRP1, CAN1, ADO1, HIS5, HIS3, ARG3, MET17, LEM3, Mnn1, Mnn9, gma12.

14. The yeast cells according to claim 13, wherein the expression cassette of α-1-2-mannosidase I is integrated into the URA3 gene, the expression cassette of N-acetyl-glucosaminyl transferase I is integrated in the ADE1 or ADE2 gene, the expression cassette of the UDP-GlcNAc transporter is integrated into the LYS2 gene, the expression cassette of α-mannosidase II is integrated into the LEU2 gene, and the expression cassette of N-acetylglucosaminyl transferase II is integrated into the CYH1 or TRP1 gene.

15. The yeast cells according to claim 1, wherein the targeting sequence in the endoplasmic reticulum or Golgi apparatus is derived from the localization sequence of the gene Mnt1 and comprises the sequence SEQ ID NO 14.

16. The yeast cells according to claim 1, wherein the terminator is derived from the CYC1 gene and comprises the sequence SEQ ID NO 15.

17. The yeast cells according to claim 3, capable of producing glycoproteins having more than 75% of a structure selected from:
Man5GlcNac2,
GlcNacMan5GlcNac2,
GlcNacMan3GlcNac2,
GlcNac2Man3GlcNac2,
Gal2GlcNac2Man3GlcNac2,
GlcNac2Man3(Fuc)GlcNac2,
Gal2GlcNac2Man3(Fuc)GlcNac2;
further comprising an integration by homologous recombination into an auxotrophy marker of an expression cassette comprising the promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively or the promoter of the Mnt1 gene, an open reading phase comprising the sequence coding for an α-1,6-fucosyl transferase FUT8, comprising a targeting sequence in the endoplasmic reticulum or Golgi apparatus and a terminator of the transcription derived from the gene CYC1 comprising the sequence SEQ ID NO 15.

18. The yeast cells according to claim 17, wherein the α-1,6-fucosyl transferase FUT8 is human and comprises the sequence SEQ ID NO 7.

19. The yeast cells according to claim 17, further comprising an integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, or the promoter SV40, an open reading phase comprising the sequence coding for a GDP-fucose transporter, notably a sequence comprising SEQ ID NO 8.

20. The yeast cells according to claim 1, wherein the α-1-2 mannosidase I is expressed under the control of the promoter pGAP and the exogenous protein glycoprotein is expressed under the control of the promoter pGAL1.

21. The yeast cells according to claim 11, capable of producing glycoproteins having more than 75% of a structure selected from NANA4Gal4GlcNac4Man3GlcNAc2 and NANA4Gal4GlcNac4(Fuc)Man3GlcNAc2, further comprising integration by homologous recombination into an auxotrophy marker of an expression cassette comprising a promoter selected from pGAP, pGAL1, PGK, TEF, adh1, nmt 1, SV40, PMA1, CaMV, pet56 of S. cerevisiae or S. pombe, and ADH2 having the sequence SEQ ID Nos. 16-26 respectively, or the promoter of the thymidine kinase of the herpes virus comprising the sequence SEQ ID NO 9, an open reading phase comprising the sequence coding for an α-2,3 sialyl transferase and the terminator derived from the CYC1 gene comprising the sequence SEQ ID NO 15.

22. The yeast cells according to claim 21, wherein the sialyl transferase is human ST4GAL4, notably a sequence comprising SEQ ID NO 10.

23. The yeast cells according to claim 1, wherein the glycoprotein is selected from the group of therapeutic glycoproteins consisting of cytokines, interleukins, growth hormones, growth factors, enzymes, monoclonal antibodies, vaccinal proteins, soluble receptors, and any type of recombinant protein.

24. The yeast cells according to claim 23, wherein the glycoproteins is EPO comprising SEQ ID NO 12.

25. A pharmaceutical composition comprising EPO as an active ingredient, said EPO having more 90% of the structure:
$NANA_2Gal_2GlcNAc_2Man_3GlcNAc_2$ or $NANA_2Gal_2GlcNAc_2Man_3(Fuc)GlcNAc_2$.

26. A culture in a fermenter comprising a basic culture medium of culture media for yeasts and a yeast cell according to claim 1.

27. A method for producing a glycoprotein having homogeneous glycan structures with more than 75% of a structure selected from:
Man5GlcNAc2,
GlcNacMan5GlcNAc2,
GlcNacMan3GlcNAc2,
GlcNac2Man3GlcNAc2,
Gal2GlcNac2Man3GlcNAc2,
NANA2Gal2GlcNac2Man3GlcNAc2,
GlcNac2Man3(Fuc)GlcNAc2,
Gal2GlcNac2Man3(Fuc)GlcNAc2,
NANA2Gal2GlcNac2Man3(Fuc)GlcNAc2,
$Gal_2GlcNAc_3Man_3GlcNAc_2$,
$NANA_2Gal_2GlcNAc_3Man_3GlcNAc_2$,
comprising the cultivation of a yeast cell according to claim 1 in a fermenter, and the extraction of said glycoprotein from the culture medium.

* * * * *